US008658617B2

(12) United States Patent
Graetz et al.

(10) Patent No.: US 8,658,617 B2
(45) Date of Patent: Feb. 25, 2014

(54) SALTS OF HIV INHIBITOR COMPOUNDS

(75) Inventors: Benjamin R. Graetz, San Mateo, CA (US); Richard Polniaszek, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 13 days.

(21) Appl. No.: 12/999,441

(22) PCT Filed: Jul. 7, 2009

(86) PCT No.: PCT/US2009/049838

§ 371 (c)(1), (2), (4) Date: Feb. 24, 2011

(87) PCT Pub. No.: WO2010/005986

PCT Pub. Date: Jan. 14, 2010

(65) Prior Publication Data

US 2011/0144050 A1 Jun. 16, 2011

Related U.S. Application Data

(60) Provisional application No. 61/078,989, filed on Jul. 8, 2008.

(51) Int. Cl.

| | |
|---|---|
| ***A61K 31/70*** | (2006.01) |
| ***C07H 19/04*** | (2006.01) |
| ***C07H 19/20*** | (2006.01) |
| ***C07C 59/265*** | (2006.01) |
| ***C07C 55/00*** | (2006.01) |

(52) U.S. Cl.

USPC ............. 514/47; 536/26.7; 562/584; 562/590

(58) Field of Classification Search

None

See application file for complete search history.

(56) References Cited

U.S. PATENT DOCUMENTS

| | | | | |
|---|---|---|---|---|
| 4,649,041 | A | 3/1987 | Peters et al. | |
| 4,665,074 | A | 5/1987 | Amschler | |
| 4,816,570 | A | 3/1989 | Farquhar | |
| 4,968,788 | A | 11/1990 | Farquhar | |
| 5,260,440 | A | 11/1993 | Hirai et al. | |
| 5,378,474 | A | 1/1995 | Morella et al. | |
| 5,413,996 | A | 5/1995 | Bodor | |
| 5,455,339 | A | 10/1995 | Chu | |
| 5,466,793 | A | 11/1995 | Honda et al. | |
| 5,493,030 | A | 2/1996 | Morgans, Jr. et al. | |
| 5,585,397 | A | 12/1996 | Tung et al. | |
| 5,633,279 | A | 5/1997 | Morgans et al. | |
| 5,654,286 | A | 8/1997 | Hostetler | |
| 5,656,745 | A | 8/1997 | Bischofberger et al. | |
| 5,663,159 | A | 9/1997 | Starrett, Jr. et al. | |
| 5,670,497 | A | 9/1997 | Bold et al. | |
| 5,744,600 | A | 4/1998 | Mansuri et al. | |
| 5,747,498 | A | 5/1998 | Schnur et al. | |
| 5,750,343 | A | 5/1998 | Maag et al. | |
| 5,750,493 | A | 5/1998 | Sommadossi et al. | |
| 5,792,756 | A | 8/1998 | Starrett, Jr. et al. | |
| 5,795,909 | A | 8/1998 | Shashoua et al. | |
| 5,811,422 | A | 9/1998 | Lam et al. | |
| 5,874,577 | A | 2/1999 | Chen et al. | |
| 5,914,332 | A | 6/1999 | Chen et al. | |
| 5,962,684 | A | 10/1999 | Vince et al. | |
| 6,018,049 | A | 1/2000 | Hajima et al. | |
| 6,072,053 | A | 6/2000 | Vince et al. | |
| 6,174,888 | B1 | 1/2001 | McQuire et al. | |
| 6,290,994 | B1 | 9/2001 | Lazaro Flores et al. | |
| 6,312,662 | B1 | 11/2001 | Erion et al. | |
| 6,319,946 | B1 | 11/2001 | Hale et al. | |
| 6,395,763 | B1 | 5/2002 | Stamos et al. | |
| 6,581,606 | B2 | 6/2003 | Kutzko et al. | |
| 6,602,902 | B2 | 8/2003 | Shashoua et al. | |
| 6,608,027 | B1 | 8/2003 | Tsantrizos et al. | |
| 6,761,903 | B2 | 7/2004 | Chen et al. | |
| 6,767,900 | B2 | 7/2004 | Ubasawa et al. | |
| 6,844,349 | B2 | 1/2005 | Kath et al. | |
| 6,858,618 | B2 | 2/2005 | Raza et al. | |
| 6,872,827 | B2 | 3/2005 | Webb et al. | |
| 6,962,684 | B2 | 11/2005 | Kawazu et al. | |
| 7,084,123 | B2 | 8/2006 | Fujikura et al. | |
| 7,169,766 | B2 | 1/2007 | Sommadossi et al. | |
| 7,358,261 | B2 | 4/2008 | Carson et al. | |
| 7,429,564 | B2 | 9/2008 | Arbit et al. | |
| 7,429,565 | B2 | 9/2008 | Boojamra et al. | |
| 7,871,991 | B2 * | 1/2011 | Boojamra et al. | 514/81 |
| 7,871,992 | B2 | 1/2011 | Jomaa et al. | |
| 8,022,083 | B2 | 9/2011 | Boojamra et al. | |
| 8,318,701 | B2 | 11/2012 | Boojamra et al. | |

(Continued)

FOREIGN PATENT DOCUMENTS

| | | |
|---|---|---|
| AU | 779816 | 10/2000 |
| DE | 4138584 | 5/1993 |

(Continued)

OTHER PUBLICATIONS

Pre-Exposure Prophylaxis, Mar. 2013, http://www.cdc.gov/hiv/prep/.*

HIV and AIDS Vaccine, 2010, http://www.avert.ord/aids0vaccine.htm.*

Office Action for New Zealand Patent Application No. 590075, mailed May 20, 2011.

Office Action for Vietnam Patent Application 1-2011-00030, mailed Jul. 5, 2011.

Alexander, J. et al. (1996) "Investigation of (Oxodioxolenyl)methyl Carbamates as Nonchiral Bioreversible Prodrug Moieties for Chiral Amines" *J. Med. Chem*. 39(2):480-486.

Anan'Eva, L.G. et al. (1983) "(2-Iodoethyl) Phosphonic Derivatives" *J. Gen. Chem, USSR* 53(3): 480-483.

Anderson, R.C. et al. (1984) "2-Chloro-4(R), 5(R)-dimethyl-2-oxo-1,3,2-dioxaphospholane, a New Chiral Derivatizing Agent" *J. Org. Chem*. 49:1304-1305.

Asante-Appiah, E. et al. (1999) "HIV-1 Integrase: Structural Organization, Conformational Changes, and Catalysis" *Advances in Virus Research* 52:351-363.

(Continued)

*Primary Examiner* — Traviss C McIntosh, III

(74) *Attorney, Agent, or Firm* — Morrison & Foerster LLP

(57) ABSTRACT

The invention is related to salts of anti-viral compounds, compositions containing such salts, and therapeutic methods that include the administration of such salts, as well as to processes and intermediates useful for preparing such salts.

21 Claims, 6 Drawing Sheets

(56) References Cited

U.S. PATENT DOCUMENTS

| | | | |
|---|---|---|---|
| 8,329,926 B2 | 12/2012 | Boojamra et al. | |
| 2001/0031773 A1 | 10/2001 | Camden | |
| 2002/0051805 A1 | 5/2002 | Ueki et al. | |
| 2002/0103378 A1 | 8/2002 | Ellis | |
| 2002/0119443 A1 | 8/2002 | Becker et al. | |
| 2002/0156133 A1 | 10/2002 | Bartholomaeus et al. | |
| 2003/0045583 A1 | 3/2003 | Hadfield et al. | |
| 2003/0109498 A1 | 6/2003 | Yuasa et al. | |
| 2003/0149044 A1 | 8/2003 | Quallich et al. | |
| 2004/0121316 A1 | 6/2004 | Birkus et al. | |
| 2004/0157793 A1 | 8/2004 | Stuyver et al. | |
| 2004/0167096 A1 | 8/2004 | Cheng et al. | |
| 2005/0037925 A1 | 2/2005 | Tsukamoto et al. | |
| 2005/0171126 A1 | 8/2005 | Torii et al. | |
| 2005/0202054 A1 | 9/2005 | Faryniarz et al. | |
| 2005/0215513 A1 | 9/2005 | Boojamra et al. | |
| 2006/0069060 A1* | 3/2006 | Redkar et al. | 514/49 |
| 2006/0079478 A1 | 4/2006 | Boojamra et al. | |
| 2006/0094870 A1 | 5/2006 | Torii et al. | |
| 2006/0223794 A1 | 10/2006 | Bourghol Hickey et al. | |
| 2006/0223820 A1 | 10/2006 | Brand et al. | |
| 2006/0281759 A1 | 12/2006 | de Diego et al. | |
| 2007/0049754 A1* | 3/2007 | Boojamra et al. | 544/243 |
| 2007/0149479 A1 | 6/2007 | Fischer et al. | |
| 2007/0149552 A1 | 6/2007 | Ku et al. | |
| 2007/0191482 A1 | 8/2007 | Choi et al. | |
| 2007/0225249 A1 | 9/2007 | Shi | |
| 2008/0207620 A1 | 8/2008 | Desai et al. | |
| 2008/0221213 A1 | 9/2008 | Christgau | |
| 2008/0226731 A1 | 9/2008 | Vasanthavada et al. | |
| 2008/0279932 A1 | 11/2008 | Reber et al. | |
| 2009/0012037 A1 | 1/2009 | Boojamra et al. | |
| 2009/0163449 A1 | 6/2009 | Wempe | |
| 2009/0202470 A1 | 8/2009 | Boojamra et al. | |
| 2009/0275535 A1 | 11/2009 | Boojamra et al. | |
| 2010/0093667 A1 | 4/2010 | Graetz et al. | |
| 2011/0288053 A1 | 11/2011 | Boojamra et al. | |
| 2013/0090299 A1 | 4/2013 | Boojamra et al. | |
| 2013/0090302 A1 | 4/2013 | Boojamra et al. | |

FOREIGN PATENT DOCUMENTS

| | | |
|---|---|---|
| EP | 0267050 | 5/1988 |
| EP | 347852 | 12/1989 |
| EP | 0369409 | 5/1990 |
| EP | 0441192 | 1/1991 |
| EP | 0465297 | 1/1992 |
| EP | 0468119 | 1/1992 |
| EP | 0468866 | 1/1992 |
| EP | 0531597 | 3/1993 |
| EP | 0 632 048 | 1/1995 |
| EP | 0 632 048 A1 | 1/1995 |
| EP | 0786455 | 7/1997 |
| EP | 0852233 | 7/1998 |
| EP | 0 919 562 A1 | 6/1999 |
| EP | 0919562 | 6/1999 |
| EP | 1295879 | 3/2003 |
| EP | 1832582 | 9/2007 |
| EP | 1832582 A1 | 9/2007 |
| EP | 1778249 | 5/2010 |
| EP | 2305680 | 4/2011 |
| EP | 2305680 A2 | 4/2011 |
| JP | 2178295 | 7/1990 |
| JP | 03005439 | 1/1991 |
| JP | 4330086 | 11/1992 |
| JP | 2007-502329 A | 2/2007 |
| RU | 2106353 | 3/1998 |
| RU | 2188203 | 8/2002 |
| WO | WO 88/06158 | 8/1988 |
| WO | WO-91/19721 | 12/1991 |
| WO | WO-91/19721 A1 | 12/1991 |
| WO | WO-92/00988 | 1/1992 |
| WO | WO-92/00988 A1 | 1/1992 |
| WO | WO 92/03452 | 3/1992 |
| WO | WO-92/13869 | 8/1992 |
| WO | WO 92/18520 | 10/1992 |
| WO | WO 93/12123 | 6/1993 |
| WO | WO-93/24510 | 12/1993 |
| WO | WO-93/24510 A1 | 12/1993 |
| WO | WO-94/21604 | 9/1994 |
| WO | WO-95/07920 | 3/1995 |
| WO | WO 96/14314 | 5/1996 |
| WO | WO-96/15111 | 5/1996 |
| WO | WO 96/40156 | 12/1996 |
| WO | WO 97/01558 | 1/1997 |
| WO | WO 98/04569 | 2/1998 |
| WO | WO 98/11906 | 3/1998 |
| WO | WO 98/15563 | 4/1998 |
| WO | WO-99/29702 A2 | 6/1999 |
| WO | WO-9929702 | 6/1999 |
| WO | WO 98/33815 | 7/1999 |
| WO | WO 99/62921 | 12/1999 |
| WO | WO 00/04033 | 1/2000 |
| WO | WO 00/52015 | 9/2000 |
| WO | WO 00/56734 | 9/2000 |
| WO | WO 01/13957 | 3/2001 |
| WO | WO 01/17982 | 3/2001 |
| WO | WO 01/19320 | 3/2001 |
| WO | WO 01/39724 | 6/2001 |
| WO | WO 01/46204 | 6/2001 |
| WO | WO 01/64693 | 9/2001 |
| WO | WO 01/96329 | 12/2001 |
| WO | WO 01/96354 | 12/2001 |
| WO | WO 02/03997 | 1/2002 |
| WO | WO 02/06292 | 1/2002 |
| WO | WO 02/08241 | 1/2002 |
| WO | WO-02/08241 A2 | 1/2002 |
| WO | WO 02/14344 | 2/2002 |
| WO | WO 02/48165 | 6/2002 |
| WO | WO 02/057425 | 7/2002 |
| WO | WO-02/057425 A2 | 7/2002 |
| WO | WO 02/100415 | 12/2002 |
| WO | WO 02/103008 | 12/2002 |
| WO | WO 03/028737 | 4/2003 |
| WO | WO-03/028737 A1 | 4/2003 |
| WO | WO 03/050129 | 6/2003 |
| WO | WO-03/050129 A1 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO-03/090690 | 11/2003 |
| WO | WO-03/091264 | 11/2003 |
| WO | WO-2004/096233 | 11/2004 |
| WO | WO 2004/096234 | 11/2004 |
| WO | WO 2004/096235 | 11/2004 |
| WO | WO-2004/096235 | 11/2004 |
| WO | WO-2004/096286 | 11/2004 |
| WO | WO 2004/096818 | 11/2004 |
| WO | WO-2005/000786 A1 | 1/2005 |
| WO | WO 2005/002626 | 1/2005 |
| WO | WO 2005/011709 | 2/2005 |
| WO | WO-2005/012324 | 2/2005 |
| WO | WO-2005/063751 | 7/2005 |
| WO | WO-2006/015261 A2 | 2/2006 |
| WO | WO-2006/015262 | 2/2006 |
| WO | WO-2006051261 A1 | 5/2006 |
| WO | WO-2006/110157 | 10/2006 |
| WO | WO-2010/005986 A1 | 1/2010 |

OTHER PUBLICATIONS

Balsiger, R.W. et al. (1959) “Synthesis of Potential Anticancer Agents. XVIII. Analogs of Carbamoyl Phosphate” *J. Org. Chem.* 24:434-436.

Balthazor, T.M. et al. (1980) “Nickel-Catalyzed Arbuzov Reaction: Mechanistic Observations” *J. Org. Chem.* 45:5425-5426.

Barre-Sinoussi, F. (1996) “HIV as the Cause of AIDS” *Lancet* 348:31-35.

Benzaria, S. et al. (1996) “Synthesis, In Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability” *J. Med. Chem.* 39:4958-4965.

(56) References Cited

OTHER PUBLICATIONS

Berge, S.M. et al. (1977) "*Pharmaceutical Salts*", Journal of Pharmaceutical Sciences, vol. 66, No. 1, pp. 1-19.
Beusen, D.D. et al. (1995) "Solid-State Nuclear Magnetic Resonance Analysis of the Conformation of an Inhibitor Bound to Thermolysin" *J. Med. Chem.* 38(14):2742-2747.
Bowker, M.J. (2002) "A Procedure for Salt Selection and Optimization". *Handbook of Pharmaceutical Salts: Properties, Selection, and Use*, Chapter 7, pp. 161-189.
Bundgaard, H. et al. (1991) "Design and Application of Prodrugs" *Textbook of Drug Design and Development* 113-191.
Burger, A. et al. (1957) "Monoesters and Ester-Amidates of Aromatic Phosphonic Acids" *J. Am. Chem. Society* 79:3575-3579.
Campagne, J. et al. (1993) "Synthesis of Mixed Phosphonate Diester Analogues of Dipeptides Using BOP or PyBOP Reagents" *Tetrahedron Letters* 34(42):6743-6744.
Campagne, J. et al. (1995) (1H-Benzotriazol-1-yloxy)tris(dimethylamino)phosphonium Hexafluorophosphate- and (1H-Benzotriazol-1-yloxy)tripyrrolidinophosphonium Hexafluorophosphate-Mediated Activation . . . *J. Org. Chem.* 60(16):5214-5223.
Campbell, D. (1992) "The Synthesis of Phosphonate Esters, an Extension of the Mitsunobu Reaction" *J. Org. Chem.* 57:6331-6335.
Carter, H.E. et al. (1965) "Carbobenzoxy Chloride and Derivatives" *Org. Synth. Coll.* 3:167-169.
Casara, P.J. et al. (1992) "Synthesis of Acid Stable 5'-O-Fluoromethyl Phosphonates of Nucleosides, Evaluation as Inhibitors of Reverse Transcriptase" *BioOrg. Med. Chem. Letters* 2(2):145-148.
Casteel, D. et al. (1991) "Steric and Electronic Effects in the Aryl Phosphate to Arylphosphonate Rearrangement" *Synthesis* 691-693.
Cavalier, J. et al. (1998) "New Highly Diastereoselective Synthesis of Phosphoramidates. A Route to Chiral Methyl p-Nitrophenyl Alkyphosphonates" *Synlett* 1:73-75.
Chen, S. et al. (1997) "Design, Synthesis, and Biochemical Evaluation of Phosphonate and Phosphonamidate Analogs of Glutathionylspermidine as Inhibitors of Glutathionylspermidine Synthetase/Amidase from *Escherichia coli" J. Med. Chem.* 40(23):3842-3850.
Coe, D.M. et al. (1991) "Synthesis of Some Mimics of Nucleoside Triphosphates" *J. Chem. Soc., Chem. Commun.* 312-314.
Coleman, R. et al. (1992) "Synthesis of the aziridino [1,2-a] pyrrolidine Substructure of the Antitumor Agents Azinomycin A and B" *J. Org. Chem.* 57(22):5813-5815.
Corey, E.J. et al. (1973) "Selective Cleavage of Allyl Ethers Under Mild Conditions by Transition Metal Reagents" *J. Org. Chem.* 38(18):3224.
D'Addona, D. et al. (2001) "Preparation of carbamates from amines and alcohols under mild conditions" *Tetrahedron Letters* 42:5227-5229.
Davies, L.C. et al. (1988) "Dinucleotide Analogues as Inhibitors of Thymidine Kinase, Thymidylate Kinase, and Ribonucleotide Reductase" *J. Med. Chem.* 31:1305-1308.
De Clercq, E. (1994) "New Developments in the Chemotherapy of Lentivirus (Human Immunodeficiency Virus) Infections: Sensitivity/Resistance of HIV-1 to Non-nucleoside HIV-1-specific Inhibitors" *Annals of the NY Academy of Sciences* 724:438-456.
De Lombaert, S. et al. (1994) "N-Phosphonomethyl Dipeptides and Their Phosphonate Prodrugs, a New Generation of Neutral Endopeptidase (NEP, EC 3.4.24.11) Inhibitors" *J. Med. Chem.* 37:498-511.
Effenberger, F. et al. (1985) "2(1H)-Pyridon als Austrittsgruppe bei Acylierungsreaktionen Anwendungen in der Peptidchemie" *Chem. Ber.* 118:468-482.
Efimov, V.A. et al. (1998) "Synthesis of DNA Analogues with Novel Carboxamidomethyl Phosphonamide and Glycinamide Internucleoside Linkages" *Bioorganic & Medicinal Chemistry Letters* 8:1013-1018.
Esposito, D. et al. (1999) "HIV Integrase Structure and Function" *Advances in Virus Research* 52:319-333.
Farquhar, D. et al. (1983) "Biologically Reversible Phosphate-Protective Groups" *J. Pharm. Sci.* 72:324-325.
Frankel, A. et al. (1998) "HIV-1 Fifteen Proteins and an RNA" *Annu. Rev. Biochem* 67:1-25.
Freeman, S. et al. (1997) "3 Prodrug Design for Phosphates and Phosphonates" *Progress in Medicinal Chemistry* 34:112-147.
Galeotti, N. et al. (1996) "A Straightforward Synthesis of Alpha—Amino Phosphonate Monoesters Using BroP or TPyCIU" Tetrahedron Letters 37(23):3997-3998.
Griffin, B. et al. (1956) "D-Glucopyranose 6-Deoxy-6-phosphonic Acid" *J. Am Chem. Society* 78(10):2336-2338.
Hakimelahi, G. et al. (1995) "Design, Synthesis, and Structure-Activity Relationship of Novel Dinucleotide Analogs as Agents Against Herpes and Human . . . " *J. Med. Chem.* 38:4648-4659.
Hansen, J. et al. (1982) "Partially Protected Polyamines" *Synthesis* 404-405.
Hildebrand, C. et al. (1992) "Sodium Salt Glycosylation in the Synthesis of Purine 2'-Deoxyribonucleosides; Studies of Isomer Distribution" *J. Org. Chem.* 57:1808-1813.
Hottiger, M. et al. (1996) "Human Immunodeficiency Virus Type 1 Reverse Transcriptase" *Biol. Chem.* 377:97-120.
Howell, H. et al. (1988) "Antiviral Nucleosides. A Stereospecific, Total Synthesis of 2'-Fluoro-2'-deoxy-beta-D-arabinofuranosyl Nucleosides" *J. Org. Chem.* 53:85-88.
International Preliminiary Report for International Application No. PCT/US2009/049838, International Filing Date Jul. 7, 2009, mailed date Jan. 11, 2011.
International Search Report and the Written Opinion for PCT/US2005/026504, Int'l Filing Date Jul. 26, 2005, mailed on Oct. 30, 2006.
International Search Report and Written Opinion for PCT/US2005/027088, Int'l Filing Date Jul. 27, 2005, mailed on Sep. 25, 2006.
Jacob III, Peyton (1982) "Resolution of (Racemic)-5-Bromonornicotine. Synthesis of (R)- and (S)-Nornicotine of High Enantiomeric Purity" *J. Org. Chem.* 47:4165-4167.
Katz, R. et al. (1994) "The Retroviral Enzymes" Annu. Rev. Biochem. 63:133-173.
Kazimierczuk, Z. et al. (1984) "Synthesis of 2'-Deoxytubercidin, 2'-Deoxyadenosine, and Related 2'-Deoxynucleosides via a Novel Direct Stereospecific Sodium Salt Glycosylation Procedure" *J. Am. Chem. Soc.* 106:6379-6382.
Khamnei, S. et al. (1996) "Neighboring Group Catalysis in the Design of Nucleotide Prodrugs" *J. Med. Chem.* 39:4109-4115.
Khandazhinskaya, A.L. et al. (2002) "Carbocyclic Dinucleoside Polyphosphonates: Interactions with HIV Reverse Transcriptase and Antiviral Activity" *J. Med. Chem.* 45:1284-1291.
Konakahara, T. et al. (1993) "A Convenient Method for the Synthesis of Activated N-Methylcarbamates" *Synthesis* 103-106.
Kunz, H. et al. (1985) "71. Synthesis of the Glycopeptide Partial Sequence A80-A84 of Human Fibroblast Interferon" *Helvetica Chimica Acta* 68:618-622.
Lee, K. et al. (1999) "Synthesis and Anti-HIV and Anti-HBV Activities of 2'-Fluoro-2',3'-unsaturated L-Nucleosides" *J. Med. Chem.* 42:1320-1328.
Lee, S. et al. (2002) "Large-Scale Aspects of Salt Formation: Processing of Intermediates and Final Products", *Handbook of Pharmaceutical Salts: Properties, Selection, and Use*, Chapter 8, pp. 191-220.
Lochmuller, C.H. et al. (1975) "Chromatographic Resolution of Enantiomers Selective Review" *Journal of Chromatography* 113:283-302.
Lu, X. et al. (1987) "Palladium-Catalyzed Reaction of Aryl Polyfluoroalkanesulfonates with O, O-Dialkyl Phosphonates" *Synthesis* 726-727.
Ma, T. et al. (1997) "Synthesis and Anti-Hepatitis B Virus Activity of 9-(2-Deoxy-2-fluoro-Beta-L-arabinofuranosyl)purine Nucleosides" *J. Med. Chem.* 40:2750-2754.
Maffre-Lafon, D. et al. (1994) "Solid Phase Synthesis of Phosphonopeptides from Fmoc Phosphonodipeptides" *Tetrahedron Letters* 35(24):4097-4098.
Marquez, V.E. et al. (1990) "Acid-Stable 2'-Fluoro Purine Dideoxynucleosides as Active Agents against HIV" *J. Med. Chem.* 33:978-985.

(56) References Cited

OTHER PUBLICATIONS

Maynard, J. A. et al. (1963) "Organophosphorus Compounds II. Preparation of Phosphonic Acid Esters Using the Dicyclohexylcarbodi-imide Reagent" *Aust. J. Chem.* 16:609-612.
McKenna, C. et al. (1979) "Functional Selectivity in Phosphonate Ester Dealkylation with Bromotrimethylsilane" *J.C.S. Chem. Comm.* 739.
Melvin, L.S. (1981) "An Efficient Synthesis of 2-Hydroxyphenylphosphonates" *Tetrahedron Letters* 22(35):3375-3376.
Mikhailopulo, I. et al. (2000) Pyrophosphoryl Derivatives of 1-(2-Deoxy-3-O-Phosphonomethyl-Beta- and -Alpha-D-erythro-Pentofuranosyl)Thymine: Synthesis and Substrate Properties Towards Some DNA Polymerases *Nucleosides, Nucleotides, and Nucleic Acids* 19(10-12):1885-1909.
Mitchell, A. et al. (1992) "Bioreversible Protection for the Phospho Group: Bioactivation of the Di(4 acyloxybenzyl) Phosphoesters . . . " *J. Chem. Soc. Perkin Trans 1* 2345-2353.
Mitsunobu, Oyo (1981) "The Use of Diethyl Azodicarboxylate and Triphenylphosphine in Synthesis and Transformation of Natural Products" *Synthesis* 1-28.
Morgan, B. et al. (1994) "Structure-Based Design of an Inhibitor of the Zinc Peptidase Thermolysin" *J. Am. Chem. Soc.* 116(8):3251-3260.
Morr, M. et al. (2001) "Formation of Phostonic Acids During the Reduction of Azidonucleosidephosphonic Acids" *Tetrahedron Letters* 42:8841-8843.
Muesing, M. et al. (1985) "Nucleic acid structure and expression of the human AIDS/lymphadenopathy retrovirus" *Nature* 313(7):450-458.
Musiol, H. et al. (1994) "Synthesis of Phosphonamidate Peptides" *J. Org. Chem.* 59(21):6144-6146.
Office Action for Vietnamese Patent Application No. 1-2011-00030, filed Jan. 5, 2011, mailing date Mar. 14, 2011.
Ohashi, K. et al. (1988) "Synthesis of Phosphonosphingoglycolipid Found in Marine Snail *Turbo cornutus*" *Tetrahedron Letters* 29(10):1189-1192.
Okamoto, Y. et al. (1990) "Optical resolution of dihydropyridine enantiomers by High-performance liquid chromatography using phenylcarbamates . . . " *Journal of Chromatography* 513:375-378.
Paquet, Alenka (1982) "Introduction of 9-fluorenylmethyloxycarbonyl, trichloroethoxycarbonyl, and benzyloxycarbonyl amine protecting groups into . . . " *Can. J. Chem.* 60:976-980.
Parang, K et al. (2000) "Novel Approaches for Designing 5'-0-Ester Prodrugs of 3'-Azido-2', 3'-Dideoxythymidine (AZT)" *Current Medicinal Chemistry* 7(10):995-1039.
Patois, C. et al. (1990) "2-Alkyl-5, 5-dimethyl-1,3,2-dioxaphosphorinan-2-ones alpha-Lithiated Carbanions. Synthesis, Stability, and Conformation" *J. Chem. Soc. Perkin Trans.* (1)1577-1581.
Petrakis, K. et al. (1987) "Palladium-Catalyzed Substitutions of Initiates Derived from Tyrosine-Containing Peptides and Simpler Hydroxyarenes Forming . . . " *J. Am. Chem. Soc.* 109:2831-2833.
Porche, D. J. (1999) "State of the Art: Antiretroviral and Prophylactic Treatments in HIV/AIDS" *Nursing Clinics of North America* 34:95-112.
Puech, F. et al. (1993) "Intracellular delivery of nucleoside monophosphates through a reductase-mediated activation process" *Antiviral Research* 22:155-174.
Pungente, M. et al. (2001) "Synthesis and Stereochemical Elucidation of a 14-Membered Ring Phosphonate" *Organic Letters* 3(5):643-646.
Quast, H. et al. (1974) "Herstellung von Methylphosphonsaure-dichlorid" *Synthesis* 490.
Redmore, Derek (1970) "Phosphorus Derivatives of Nitrogen Heterocycles. 2. Pyridinephosphonic Acid Derivatives" *J. Org. Chem.* 35(12):4114-4117.
Roach et al. (1987) "Fluorescence Detection of Alkylphosphonic Acids Using p-(9-Anthroyloxy)phenacyl Bromide" *Analytical Chem.* 59:1056-1059.
Rosenberg, I. et al. (1987) "Synthesis of Potential Prodrugs and Metabolites of 9-(S)-(3-Hydroxy-2-Phosphonylmethoxypropyl) Adenine" *Collect. Czech. Chem. Commun.* 52:2792-2800.
Saady, M. et al. (1995) "Selective Monodeprotection of Phosphate, Phosphite, Phosphonate, and Phosphoramide Benzyl Esters" *J. Org. Chem.* 60:2946-2947.
Schon, I. et al. (1986) "9-Fluorenylmethyl Pentafluorophenyl Carbonate as a Useful Reagant for the Preparation of N-9-Fluorenylmethyloxycarbonylamino . . . " *Synthesis* 303-305.
Serafinowska, H. et al. (1995) "Synthesis and in Vivo Evaluation of Prodrugs of 9-[2-(Phosphonomethoxy)ethoxy]adenine" *J. Med. Chem.* 38:1372-1379.
Sharma, S. et al. (1989) "Spermexatin and Spermaxatol: New Synthetic Spermidine-Based Siderophore Analogues" *J. Med. Chem.* 32:357-367.
Shirokova, E.A. "New Lipophilic Derivatives of AZT and d4T 5'-Phosphonates," (2003) *Nucleosides, Nucleotides and Nucleic Acids* 22(5-8):981-985.
Siddiqui, A .Q. et al. (1999) "The Presence of Substituents on the Aryl Moiety of the Aryl Phosphoramidate Derivative of D4T Enhances Anti-HIV Efficacy in Cell Culture: A Structure-Activity Relationship" *Journal of Medicinal Chemistry* 42(3):393-399.
Silverberg, L. et al. (1996) "A Simple, Rapid and Efficient Protocol for the Selective Phosphorylation of Phenols with Dibenzyl Phosphite" *Tetrahedron Letters* 37(6):771-774.
Smith, M. et al. (1994) "Development and significance of nucleoside drug resistance in infection caused by the human immunodeficiency virus type 1" *Clin. Invest. Med.* 17(3):226-243.
Smith, R. et al. (2003) "A novel MyD-1 (SIRP-1) signaling pathway that inhibits LPS-induced TNF production by monocytes" *Blood* 102(7):2532-2540.
Stahl, P.H. (2002), "*Appendix*," Handbook of Pharmaceutical Salts: Properties, Selection, and Use, pp. 329-350.
Stahl, P.H. et al. (2002) "*Monographs on Acids and Bases*", Handbook of Pharmaceutical Salts: Properties, Selection, and Use, Chapter 12, pp. 265-327.
Stamm, H. et al. (1980) "Reactions with Aziridines XXI The (Michaelis-) Arbuson Reaction with N-Acyl Aziridines and Other Amidoethylations at Phosphorus" *Tetrahedron Letters* 21:1623-1626.
Sun, C. et al. (2002) "A General Synthesis of Dioxolenone Prodrug Moieties" *Tetrahedron Letters* 43:1161-1164.
Szabo, T. et al. (1995) "Solid Phase Synthesis of 5'-Methylenephosphonate DNA" *Nucls. & Nuclt.* 14(3-5):871-874.
Tang, T. et al. (1999) "The tert-Butanesulfinyl Group: An Ideal Chiral Directing Group and Boc-Surrogate for the Asymmetric Synthesis and Applications of . . . " *J. Org. Chem.* 64:12-13.
Tarrago-Litvak, L. et al. (1994) "The reverse transcriptase of HIV-1: from enzymology to therapeutic intervention" *The FASEB Journal* 8:497-503.
Thomson, W. et al. (1993) "Synthesis and Bioactivation of Bis(aroyloxymethyl) and Mono(aroyloxymethyl) Esters of Benzylphosphonate and . . . " *J. Chem. Soc. Perkin Trans.* 19:2303-2308.
Van Der Laan, A.C. et al. (1996) "An Approach Towards the Synthesis of Oligomers Containing a N-2 Hydroxyethyl-aminomethylphosphonate Backbone: A Novel PNA Analogue" *Tetrahedron Letters* 37(43):7857-7860.
Van Der Laan, a.C. et al. (1998) "Optimization of the Binding Properties of PNA-(5')-DNA Chimerae" *Bioorg. Med. Chem. Letters* 8:663-668.
Vieira De Almeida, M. et al. (1999) "Synthesis of Deoxy Phosphatidylinositol Analogues and Phosphonate Isosters of Ins(1,4,5)$P_3$" *Tetrahedron Letters* 55:12997-13010.
Von Der Helm, K. (1996) "Retroviral Proteases: Structure, Function and Inhibition From a Non-Anticipated Viral Enzyme to the Target of a Most Promising HIV Therapy" *Biol. Chem.* 377:765-774.
Watanabe, Y. et al. (1988) "Dibenzyl Phosphorofluoridate, A New Phosphorylating Agent" *Tetrahedron Letters* 29(45):5763-5764.

(56) References Cited

OTHER PUBLICATIONS

Wermuth, C.G. et al. (2002) "*Selected Procedures for the Preparation of Pharmeaceutically Acceptable Salts*", Handbook of Pharmaceutical Salts: Properties, Selection, and Use, Chapter 11, pp. 249-263.
Wessig, P. et al. (1997) "A Convenient One-Pot Conversion of N-Boc-B-Aminoalcohols into N-Boc-Aziridines" *Synlett* 8:893-894.
Wissner, A. et al. (1992) "Analogues of Platelet Activating Factor. 6 Mono- and Bis-Aryl Phosphate Antagonists of Platelet Activating Factor" *J. Med. Chem.* 35:1650-1662.
Yamauchi, K. et al. (1984) "Synthesis of Peptides Analogues Containing (2-aminoethyl)phosphonic acid(ciliatine)" *J. Org. Chem.* 49(7):1158-1163.
Zemlicka, J. et al. (1972) "Nucleosides. XV. Decarboxylative Elimination of 2'-Deoxynucleodise Uronic Acids" *J. Am. Chem. Soc.* 94(9):3213-3218.
Office Action for European Patent Application No. 09790117.7-2101, mailing date Mar. 8, 2011.
Abdel-Meguid, Sherin S. et al., "Inhibition of Human Immunodeficiency Virus-1 Protease by a C.sub.2-Symmetric Phosphinate. Synthesis and Crystallographic Analysis", *Biochemistry*, vol. 32, No. 31, 7972-7980, (1993).
Allen, Lee F. et al., "CI-1040 (PDI84352), a Targeted Signal Transduction Inhibitor of MEK (MAPKK)", *Seminars in Oncology*, vol. 30, No. 5, Supp. 16, Elsevier Inc., 105-116, (2003).
Bantia, Shanta et al., "Purine nucleoside phosphorylase inhibitor BCX-1777 (Immucillin-H)—a novel potent and orally active immunosuppressive agent", *International Immunopharmacology*, vol. 1, 1199-1210, (2001).
Beauchamp, Lilia M., et al., "Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase", *Journal of Medicinal Chemistry*, vol. 39, 949-956, (1996).
Birkus et al. "Cathepsin A is the Major Hydrolase Catalyzing the Intracellular Hydrolysis of the Antiretroviral Nucleotide Phosphonoamidate Prodrugs GS-7340 and GS-9131," vol. 51, No. 2, pp. 543-550, (2007).
Borhani et al., "A-420983: a potent, orally active inhibitor of Ick with efficacy in a model of transplant rejection", *Bioorganic & Medicinal Chemistry Letters*, vol. 14, 2613-2616, (2004).
Bundgaard, Design of Prodrugs, 70-74, (1985).
Bzowska, Agnieszka et al., "Purine nucleoside phosphorylases: properties, functions, and clinical aspects", *Pharmacology & Therapeutics*, vol. 88, 349-425, (2000).
Chapman, H. et al., "Practical Synthesis, Separation, and Stereochemical Assignment of the PMPA Pro-Drug GS-7340", *Nucleosides, Nucleotides & Nucleic Acids*, vol. 20, Nos. 4-7, 621-628, (2001).
Chong, Y., et al., "Effects of fluorine substitution of cytosine analogues on the binding affinity to HIV-1 reverse transcriptase", *Bioorganic & Medicinal Chemistry Letters*, 14, 437-440, (2004).
Clark et al., "Mycophenolic Acid Analogues as Potential Agents Against West Nile Virus Infection", Dept. of Chemistry, Pharmasset, 1860 Montreal Road, Tucker, GA 30084, 1 page, (2003).
Conklyn et al., "The JAK3 inhibitor CP-690550 selectively reduces NK and CD8+ cell numbers in cynomolgus monkey blood following chronic oral dosing", *Journal of Leukocyte Biology*, vol. 76, 1-8, (2004).
De Clercq, "New Developments in Anti-HIV Chemotherapy", *Current Medicinal Chemistry*, vol. 8, No. 13, 1543-1572, (2001).
De Clereq, "Highlights in the Development of New Antiviral Agents", *Mini Reviews in Medicinal Chemistry*, vol. 2, No. 2, 163-175, (2002).
Dvorakova et al., "Synthesis of 2'-Aminomethyl Derivatives of N-(2-(Phosphonomethoxy)ethyl) Nucleotide Analogues as Potential Antiviral Agents", *J. Med. Chem.*, vol. 38, No. 17, 3263-3268, (1996).
Evans, "Exploring Structure—Activity Relationships of Transition State Analogues of Human Purine Nucleoside Phosphorylase", *J. Med. Chem.*, vol. 46, No. 15, 3412-3423, (2003).
Gobec et al., "Phosphonate inhibitors of antiget 85C, a crucial enzyme involved in the biosynthesis of the *Mycobacterium tuberculosis* cell wall", *Bioorganic and Medicinal Chemistry Letters*, vol. 14, 3559-3562, (2004).
Hartmann et al., "Toxicity associated with high dosage 9-[(2R,5R-2,5-dihydro-5-phosphonomethoxy)-2-furanyl]adenine therapy and attempts to abourt early FIV infection", *Antiviral Research* 36, 11-25, (1997).
Hegedus et al., "Synthesis of 4'-Methyl and 4'-cyano Carbocyclic 2',3'-Didehydro Nucleoside Analogues via 1,4-Addition to Substituted Cyclopentenones", *J. Org. Chem.*, vol. 69, No. 24, 8492-8495, (2004).
Herczegh et al., "Osteoadsorptive bisphosphonate derivatives of fluoroquinolone antibacterials", J. Med. Chem., vol. 45, 2338-2341, (2002).
Hirabayashi et al., "Bone-Specific Drug Delivery Systems", *Clinical Pharacokinetics*, vol. 42, No. 15, 1320-1330, (2003).
Holy et al., Synthesis of N-(2-Phosphonylmethoxyethyl) Derivatives of Heterocyclic Bases *Collect. Czech. Chem. Commun.*, vol. 54, 2190-2210 (1989).
Hostetler, "Nucleotides for topical treatment of psoriasis", CAS:127:185859, 2 pages, (1997).
Jahne et al., "Preparation of Carbocyclic Phosphonate Nucleosides", *Tetrahedron Letters*, 33(37), 5335-5338 (1992).
Jain et al., "Characterization of Pharmacological Efficacy of VX-148, a New, Potent Immunosuppressive Inosine 5'-Monophosphate Dehydrogenase Inhibitor", *Journal of Pharmacology and Experimental Therapeutics*, vol. 302, No. 3, 1272-1277, (2002).
Karpenko et al., "Synthesis and Antitherpetic Activity of Acyclovir Phosphonates", *Nucleosides, Nucleotides & Nucleic Acids*, vol. 22, No. 3, 319-328, (2003).
Kato et al., "Enantio- and diastereoselective syntheis of 4'-.alpha.-substituted carbocyclic nucleosides", *Tetrahedron: Asymmetry*, vol. 9, 911-914, (1998).
Kato et al., Stereoselective synthesis of 4'-.alpha.-alkycicarbovir derivatives based on an asymmetric synthesis or chemo-enzymatic procedure, *Chemical & Pharmaceutical Bulletin*, vol. 49, No. 9, 1256-1264, (1999).
Kilpatrick et al., "Intravenous and oral pharmacokinetic study of BCX-1777, a novel purine nucleoside phosphorylase transition-state inhibitor, In vivo effects on blood 2'-deoxyguanosine in primates", International Immunopharmacology, vol. 3, 541-548, (2003).
Kim et al., "Regiospecific and Highly Stereoselective Electrophilic Addition to Furanoid Glycals: Synthesis of Phosphonate Nucleotide Analogues with Potent Activity against HIV", *J. Org. Chem.*, vol. 56, No. 8, 2642-2647, (1991).
Kinsky et al., "Effect of liposomes sentitized with methotrexate-.gamma.- dimyristoylphosphatidylethanolamine on cells that are resistant to methotrexate", Biochimica et Biophysica Acta, vol. 885, 129-135, (1986).
Kinsky et al., "Circumvention of the methotrexate transport system by methotrexate-phosphatidylethanolamine derivatives effect of fatty acid chain length", *Biochimica et Biophysica Acta*, vol. 921, 96-103, (1987).
Kinsky et al., "Inhibition of cell proliferation by putative metabolites and non-degradable analogs of methotrexate-.gama.-dimyristoylphosphatidylethanolamine", *Biochimica et Biphysica Acta*, vol. 917, No. 2, 211-218, (1987).
Ko, Ok Hyun et al., "Efficient synthesis of novel carbocyclic nucleosides via sequential Claisen rearrangement and ring-closing metathesis", *Tetrahedron Letters*, vol. 43, 6399-6402, (2002).
Krayevsky et al., "5'-Hydrogenphosphonates and 5'-methylphosphonates of sugar-modified pyrimidine nucleosides as potential anti-HIV-1 agents", *Nucleosides & Nucleotides*, 11(2-4), 177-196, (1992).
Lee et al., "Structure-Activity Relationships of 2'-Fluoro-2',3'-unsaturated D-Nucleosides as Anti-HIV-1 Agents", *J. Med. Chem.*, 45, 1313-1320, (2002).
Leff et al., "Antidiabetic PPAR.gamma. Ligands: An update on Compounds in development", *Curr. Med. Chem.—Imun., Endoc. & Metab. Agents*, vol. 2, No. 1, 33-47, (2002).

(56) References Cited

OTHER PUBLICATIONS

Lewandowicz et al., "Achieving the Ultimate Physiological Goal in Transition State Analogue Inhibitors for Purine Nucleoside Phosphorylase", The Journal of Biological Chemistry, vol. 278, No. 34, 31454-31468, (2003).
Mackman et al. "Discovery of GS-9131: Design, synthesis and optimization of amidate prodrugs of the novel nucleoside phosphonate HIV reverse transcriptase (RT) inhibitor GS-9148", *Bioorganic & Medicinal Chemistry*, vol. 18, 3606-3617, (2010).
Margolin et al., "AMP Deaminase as a Novel Practical Catalyst in the Synthesis of 6-Oxopurine Ribosides and Their Analogs", *Journal of Organic Chemistry*, 59(24), 7214-7218 (1994).
Menendez-Arias, Luis et al., "Targeting HIV: antiretroviral therapy and development of drug resistance", *TRENDS in Pharmacological Sciences*, vol. 23, No. 8, 381-388, (2002).
Morgans, et al., "5-Substituted derivatives of mycophenolic acid", CAS: 124:86709 (1995).
Ono-Nita, Suzane Kioko et al., "Novel Nucleoside Analogue MCC-478 (LY582563) Is Effective against Wild-Type or Lamivudine-Resistant Hepatitis B Virus", *Antimicrobial Agents and Chemotherapy*, vol. 46, No. 8, 2602-2605, (2002).
Pankiewicz et al., "Novel Mycophenolic Adenine Bis(phosphonate) Analogues as Potential Differentiation Agents against Human Leukemia", *J. Med. Chem.*, vol. 45, No. 3, 703-712, (2002).
Pauwels et al., "Investigations on the Anti-HIV Activity of 2', 3'-Dideoxyadenosine Analogues with Modifications in Either the Pentose or Purine Moiety", *Biochemical Pharmacology*, vol. 37, No. 7, 1317-1325, (1988).
Prashad, Mahavir et al., "An Efficient and Large-Scale Enantioselective Synthesis of PNP405: A Purine Nucleoside Phosphorylase Inhibitor", *J. Org. Chem.*, vol. 67, No. 19, 6612-6617, (2002).
Ray et al., "Role of Purine Nucleoside Phosphorylase in Interactions between 2', 3'-Dideoxyinosine and Allopurinal, Ganciclovir, or Tenofovir", Antimicrobial Agents and Chemotherapy, vol. 48, No. 4, 1089-1095, (2004).
Ray et al. "Intracellular Metabolism of the Nucleotide Prodrug GS-9131, a Potent Anti-Human Immunodeficiency Virus Agent," vol. 52, No. 2, pp. 648-654, (2008).
Roberts, Stanley M., "Development of the route to the new anti-AIDS drug abacavir: A highlight of academic/industry laison", *IDrugs*, vol. 1, No. 8, 896-899, (1998).
Rosowsky et al., "Methotrexate Analogues—27", *Biochemical Pharmacology*, vol. 35, No. 19, 3327-3333, (1986).
Rosowsky et al., "Methotrexate Analogues, 32, Chain Extension, .alpha.-Carboxyl Replacement by Sulfonate and Phosphonate: Effect on Enzyme Binding and Cell-Growth Inhibition", *J. Med. Chem.*, vol. 31, No. 7, 1326-1331, (1988).
Schultz, "Prodrugs of biologically active phosphate esters", *Bioorganic & Medicinal Chemistry*, vol. 11, 885-898, (2003).
Sekiya et al., "2-Amino-6-arylthio-9-2-(phosphonomethoxy) ethyl) purine Bis(2,2,2-trifluoroethyl) Esters as Novel HBV-Specific Antiviral Reagents", *Journal of Medicinal Chemistry*, vol. 45, No. 14, American Chemical Society, 3138-3142, (2002).
Shi et al., "*Plasmodium falciparum* Purine Nucleoside Phosphorylase", *The Journal of Biological Chemistry*, vol. 279, No. 18, 18103-18106, (2004).
Sintchak et al., "The structure of inosine 5'-monophosphate dehydrogenase and the design of novel inhibitors", *Immunopharmachology*, vol. 47, 163-184, (2000).
Squires, "An introduction to nucleoside and nucleotide analogues", *Antiviral Therapy*, 6(*Suppl*.3), 1-14, (2001).
Srinivas et al., "Metabolism and In Vitro Antiretroviral Activities of Bis(Pivaloyloxymethyl) Prodrugs of Acyclic Nucleoside Phosphonates", *Antimicrobial Agents and Chemotherapy*, vol. 37, No. 10, American Society for Microbiology, 2247-2250, (1993).
Sturtz et al., "Amethopterine (methotrexate) phosphonoglutamic acid analogs. Part II. Dihydrofolate reductase inhibition" CAS:101:143560, 1 page, (1984).
Sturtz et al., "Analogues phosphonoglutamiques d'amethopterine (methotrexate)", *Eur. J. Med. Chem—Chim. Ther*., vol. 19, No. 3, 267-273, (1984). [English Abstract on first page.].
Sturtz et al., "Su rune nouvelle approche de pharmacomodulation du methotrexate: synthese d'analogues gem-diphosphoniques d'amethopterine et de la N-10 deaza amethopterine", *Medicinal Chemistry, C. R. Acad. Sci. Paris*, vol. 10, No. 2, Academie des Sciences, 739-742, (1990). [English Abstract on first page.].
Sturtz et al., "A study of the delivery-targeting concept applied to antineoplasic drugs active on human osteosarcoma, I. Synthesis and biological activity in nude mice carrying human osteosarcoma xenografts of gem-bisphosphonic methotrexate analogues", Eur J. Med. Chem., vol. 27, No. 8, 825-833, (1992).
Sturtz et al., "Synthesis of gem-bisphosphonic methotrexate conjugates and their biological response towards Walker's osteosarcoma", Eur. J. Med. Chem., vol. 28, 899-903, (1993).
TRUVADA® label revision approved on Jul. 16, 2012, NDA No. 021752, Reference ID 3159758, 38 pages.
Vielhaber, Bernd, Bericht vom 3rd International Workshop on Salvage Therapy for HIV-Infection, Deutsche Aids-Hilfe e.V. FaxReport zu HIV and AIDS, 12-14, (2000). [English translation of Abstract—4 pages].
Waegell et al. "A420983, a novel, small molecule inhibitor of LCK prevents allograft rejection", Transplantation Proceedings, vol. 34, 1411-1417, (2002).
Wroblewski et al., "Synthesis of (1R,2S)- and (1S,2S)-3-(4-carbamoy1-1,2,3-triazol-1-yl)-1,2-dihydroxypropylphosphonate-s", Tetrahedron: Asymmetry, vol. 15, 1457-1464, (2004).
Bundgaard, Hans, Design of Prodrugs, (1985), pp. 70-74.
Chapman, H. et al., Practical Synthesis, Separation and Stereochemical Assignment of the PMPA Pro-Drug GS-7340, Nucleosides, *Nucleotides & Nucleic Acids*, (2001), pp. 621-627, vol. 20, Nos. 4-7, Marcel Dekker, Inc.
Chong, Y. et al. (2002) "Stereoselective Synthesis and Antiviral Activity of D-2',3'-Didehydro-2',3'-dideoxy-2'-fluoro-4'-thionucleosides" *J. Med. Chem*. 45:4888-4898.
Eisenberg, E.J. et al. (2001) "Metabolism of GS-7340, a Novel Phenyl Monophosphoramidate Intracellular Prodrug of PMPA in Blood" *Nucleosides, Nucleotides and Nucleic Acids* 20(4-7):1091-1098.
Gumina, Giuseppe et al., Advances in Antiviral Agents for Hepatitis B Virus Antiviral *Chemistry & Chemotherapy*,( 2001), 93-117, vol. 12, Suppl. International Medical Pres.
Handbook of Pharmaceutical Salts;(2002), Chapter 5, Control of the Crystallization Process; pp. 214, 254 and 255.
Herdewijn, P. et al. (1987) "3'-Substituted 2', 3'-Dideoxynucleoside Analogues as Potential Anti-HIV (HTLV-III/LAV) Agents" *J. Med. Chem*. 30:1270-1278.
International Search Report for PCT/US2004/013063 Int'l Filing Date Apr. 26, 2004 mailed on Apr. 13, 2005.
International Search Report for PCT/US2005/027088, Int'l Filing Date Jul. 27, 2005, mailed on Sep. 25, 2006.
International Search Report for PCT/US2005/026504, Int'l Filing Date Jul. 26, 2005, mailed on Oct. 30, 2006.
International Search Report for PCT/US2009/049838 Int'l Filing Date Jul. 7, 2009 mailed on Oct. 10, 2009.
Jahne, et al., "Preparation of Carbocyclic Phosphonate Nucleosides", *Tetrahedron Letters*, 33(37), 5335-5338 (1992).
Jeong, L.S. et al. (2003) "Design, Synthesis, and Biological Evaluation of Fluoroneplanocin A as the Novel Mechanism-Based Inhibitor of S-Adenosylhomocysteine Hydrolase" *Journal of Medicinal Chemistry* 46(2): 201-203.
Karpenko, Inna L., et al., Synthesis and Antitherpetic Activity of Acyclovir Phosphonates, *Nucleosides, Nucleotides & Nucleic Acids*, (2003), 319-328, vol. 22, No. 3, Marcel Dekker, Inc.
Kim, Choung Un et al., Regiospecific and Highly Stereoselective Electrophilic Addition to Furanoid Glycals: Synthesis of Phosphonate Nucleotide Analogues with Potent Activity Against HIV, *J. Org. Chem*., (1991), 2642-2647, vol. 56, No. 8, American Chemical Society.
Lee, "Synthesis and Anti-HIV and Anti-HBV Activities of 2'-Fluoro-2',3'-unsaturated L-Nucleosides", *Journal of Medicinal Chemistry* (1999), 42(7), 1320-1328.

(56) References Cited

OTHER PUBLICATIONS

Margolin, et al, "AMP Deaminase as a Novel Practical Catalyst in the Synthesis of 6-Oxopurine Ribosides and Their Analogs", *Journal of Organic Chemistry*, 59(24), 7214-7218 (1994).
Moon, H.R. et al. (2002) "Synthesis of 2', 3'-didehydro-2',3'-dideoxy-2'-fluoro apionucleosides as potential antiviral agents" *J. Chem. Soc., Perkin Trans*. 1:1800-1804.
Ono-Nita, Suzane Kioko, et al., "Novel Nucleoside Analogue MCC-478 (LY582563) Is Effective Against Wild-Type or Lamivudine-Resistant Hepatitis B Virus", *Antimicrobial Agents and Chemotherapy*, vol. 46, No. 8, 2602-2605 (2002).
Parang, K et al. (2000) "Novel Approaches for Designing 5'-0-Ester Prodrugs of 3'-Azido-2', 3'-Dideoxythymidine (AZT)" *Current Medicinal Chemistry* (2000), 995-1039, vol. 7, No. 10, Bentham Science Publishers Ltd.
Remington Farmacia (Ramington Pharmacy); 1998 , 19 Edition, Chapters 20, 83 and 91.
Sekiya, Kouichli et al., 2-Amino-6-arylthio-9-2-(phosphonomethoxy) ethyl) purine Bis(2,2,2-trifluoroethyl) Esters as Novel HBV-Specific Antiviral Reagents, Journal of Medicinal Chemistry, (2002), 3138-3142, vol. 45, No. 14, American Chemical Society.
Shirokova, E.A. "New Lipophilic Derivatives of AZT and d4T 5'-Phosphonates," (2003) *Nucleosides, Nucleotides and Nucleic Acids* 22 5-8 :981-985.
Siddiqui, A.Q. et al. (1999) "The Presence of Substituents on the Aryl Moiety of the Aryl Phosphoramidate Derivative of D4T Enhances Anti-HIV Efficacy in Cell Culture: A Structure-Activity Relationship" *Journal of Medicinal Chemistry* 42(3):393-399.
West, Solid-State Chemistry and Its Applications, John Wiley & Sons, 3 pages, (1984).
Zhou, W. et al. (2004) "Synthesis, Structure-Activity Relationships, and Drug Resistance of beta-D-3'-Fluoro-2',3'-Unsaturated Nucleosides as Anti-HIV Agents" *J. Med. Chem*. 47:3399-3408.
U.S. Office Action for U.S. Appl. No. 12/999,441 dated Mar. 28, 2013.
U.S. Office Action for U.S. Appl. No. 12/999,441 dated Aug. 28, 2012.
Peru Office Action for Patent Application No. 6.2011 dated Jul. 4, 2012 (English Translation of the Office Action).
New Zealand Office Action for Patent Application No. 590075 dated Jul. 15, 2011 (English Translation of the Office Action).
Mexico Office Action for Patent Application No. MX/a/2011/000306 dated May 22, 2012 (English Translation of the Office Action).
Israel Office Action for Patent Application No. 210006 dated May 5, 2012 (English Translation of the Office Action).
Colombia Office Action for Patent Application No. 10-159.887 dated Feb. 6, 2013 (English Translation of the Office Action).
China Office Action for Patent Application No. 200980126248.X dated Mar. 17, 2013 (English Translation of the Office Action).
Taiwan Office Action for Patent Application No. 094125503 dated Jul. 8, 2011 (English Translation of the Office Action).
U.S. Office Action for U.S. Appl. No. 11/658,628 dated Dec. 15, 2011.
U.S. Office Action for U.S. Appl. No. 11/658,628 dated Apr. 28, 2011.
Poland Office Action for Patent Application No. P382843 dated Oct. 5, 2011(English Translation of the Office Action).
Mexico Office Action for Patent Application No. MX/a/2010/007924 dated Feb. 16, 2012 (English Translation of the Office Action).
India Office Action for Patent Application No. 1211/DELNP/2007 dated Mar. 29, 2012 (English Translation of the Office Action).
Eurasian Office Action for Patent Application No. 200700363 dated Aug. 24, 2011 (English Translation of the Office Action).
U.S. Office Action for U.S. Appl. No. 13/187,293 dated Sep. 24, 2012 (English Translation of the Office Action).
Japanese Office Action mailed on Dec. 18, 2013, for Japanese Patent Application No. 2011-517525, filed Jul. 7, 2009, four pages.
Kojima, T. et al. (Apr. 2006). "Crystalline Form Information From Multiwell Plate Salt Screening by Use of Raman Microscopy," *Pharm. Res.* 23(4):806-812.

* cited by examiner

SALTS OF HIV INHIBITOR COMPOUNDS

FIELD OF THE INVENTION

The invention relates generally to salts of compounds with antiviral activity and more specifically with anti-HIV properties.

BACKGROUND OF THE INVENTION

Human immunodeficiency virus (HIV) is a retrovirus that can lead to acquired immunodeficiency syndrome (AIDS), a condition in humans in which the immune system is weakened, leading to life-threatening opportunistic infections. Inhibitors of HIV are useful to treat HIV infection in a mammal (e.g., reduce and limit the establishment and progression of infection by HIV) as well as in diagnostic assays for HIV. The usefulness of currently marketed inhibitors of HIV is to some extent limited by toxicity and other side effects. Thus, there is a need for new HIV therapeutic agents.

A pharmaceutical formulation of a therapeutic agent must reproducibly and consistently deliver the therapeutic agent to a patient in need thereof. This consistency of delivery can be achieved, at least in part, by incorporation of a stable, soluble, solid-state form of the therapeutic agent into the pharmaceutical composition. Moreover, the synthesis of the desired solid-state form of the therapeutic agent should be technically and economically feasible, and should be suitable for full-scale commercial production.

SUMMARY OF THE INVENTION

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a reverse transcriptase inhibitor that blocks the replication of HIV viruses, in vivo and in vitro, and has limited undesirable side effects when administered to human beings. The structure of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is shown in Formula P:

(P)

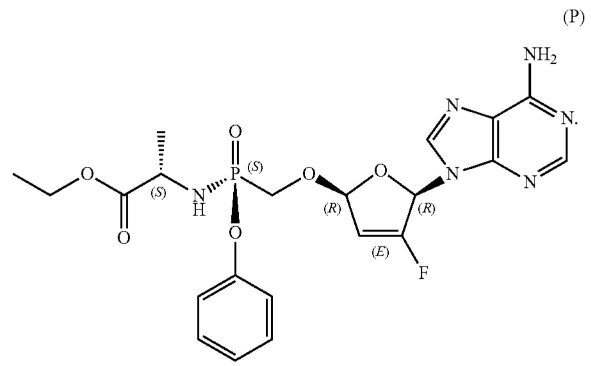

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a low melting point, amorphous, solid which is difficult to isolate, purify, store for an extended period, and formulate as a pharmaceutical composition. Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is also a weak base that is capable of forming salts with acids. Accordingly, in one aspect, the present invention provides stable salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate that are more physically stable, and are more readily isolated and formulated, than the free base form of the compound.

The salts of the present invention are useful, for example, for treating human patients infected with human immunodeficiency virus (strains of HIV-1 or HIV-2) which causes AIDS. The salts of the present invention are also useful, for example for preparing a medicament for treating HIV or an HIV associated disorder. The salts of the present invention are also useful, for example, for inhibiting the replication of HIV viruses in vitro, and can be used, therefore, in biological assays as a control compound for identifying other reverse transcriptase inhibitors, or for investigating the mechanism of action of HIV reverse transcriptase and its inhibition.

Thus, in one aspect, the present invention provides citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, and methods of making the foregoing salts. In some embodiments, the salts of the present invention are anhydrous, while in other embodiments the salts of the present invention are at least partially hydrated. In some embodiments, the salts of the present invention exist as crystalline forms.

Thus, the present invention comprises citrate, succinate and malonate salts of the compound of Formula P, as well as hydrates thereof. The inventive hydrates may be in a partial (e.g., hemi-hydrate) or full hydrated state (e.g., mono-hydrate). The present invention also comprises the subject salts in anhydrous or essentially anhydrous states. Similarly, the inventive salts and hydrates thereof comprise amorphous and crystalline states, as well as states comprising both amorphous and crystalline characteristics. As used herein, "crystalline" means a material that has an ordered, long range molecular structure. In contrast, "amorphous" materials do not possess long range order. It is understood that crystalline materials are generally more stable thermodynamically than amorphous forms of the same substance. Thus, with only a few notable exceptions, it is generally preferred to use crystalline materials in pharmaceutical applications. A measure of the degree of crystallinity of the inventive compounds can be seen, for example, in the sharpness of the DSC and XRPD absorption bands (peaks). The sharper the peak, the higher the degree of crystallinity. Conversely, the broader the peak, the lower the degree of crystallinity.

As described more fully in Example 12 herein, in specific embodiments, a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from an X-ray powder diffraction pattern, at spectral d-spacings of 4.48, 3.12 and 6.05 angstroms; a succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from an X-ray powder diffraction pattern, at spectral d-spacings of 3.57, 4.80 and 4.99 angstroms; and a malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is characterized by absorption bands, obtained from X-ray powder diffraction pattern, at spectral d-spacings of 4.99, 5.93 and 4.72 angstroms. In another specific embodiment, the present invention provides a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate having a melting point of from 142° C. to 150° C.

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is an amidate prodrug which undergoes reaction with and decomposition in protic solvents. The rate of the reaction depends on pH and temperature. Consequently, the formation of a stable salt between the amidate prodrug and citric acid, succinic acid and/or malonic acid, which each contain nucleophilic moieties capable of reacting with the prodrug (e.g., reaction with the amidate moiety of the prodrug) is a surprising and unexpected result.

In another aspect, the present invention provides pharmaceutical compositions that each include a therapeutically effective amount of a salt of the present invention and a pharmaceutically acceptable carrier or excipient. Pharmaceutical compositions of the present invention may also include an additional therapeutic agent, such as an antiviral, antibacterial, antifungal or anticancer agent. The pharmaceutical compositions of the invention may be in the form of unit dosage forms, such as tablets or capsules. The unit dosage forms typically provide an effective daily dose of a salt of the present invention to a human being in need thereof. Effective daily doses of the salts of the present invention are typically from 1 mg to 100 mg, such as from 10 mg to 30 mg.

In another aspect, the present invention provides methods of making the citrate, succinate and malonate salts of the present invention. Thus, for example, the present invention provides a process for preparing a citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., acetonitrile) with form about one equivalent to about 1.2 equivalents of citric acid at a temperature in the range of from about 55° C. to about 75° C.

The present invention also provides a process for preparing a succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., 2-butanone) with from about one equivalent to about 1.2 equivalents of succinic acid at a temperature in the range of from about 60° C. to about 70° C. to form the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

Further, the present invention provides a process for preparing a malonate salt of Ethyl N—[(S)({[(2R,5R)-5-(6-amino-9H-purin-9-yl)-4-fluoro-2,5-dihydrofuran-2-yl]oxy}methyl) phenoxyphosphinoyl]-L-alaninate, wherein the process includes the step of contacting about one equivalent of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate free base in a suitable solvent (e.g., 2-butanone) with from about one equivalent to about 1.2 equivalents of malonic acid at a temperature in the range of from about 50° C. to about 70° C. to form the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

In a further aspect, the present invention provides methods of treating or prophylactically preventing AIDS, wherein the methods include the step of administering to a human being suffering from AIDS a therapeutically effective amount of a salt of the invention, or a hydrate thereof.

DETAILED DESCRIPTION OF EXEMPLARY EMBODIMENTS

Figure 1:
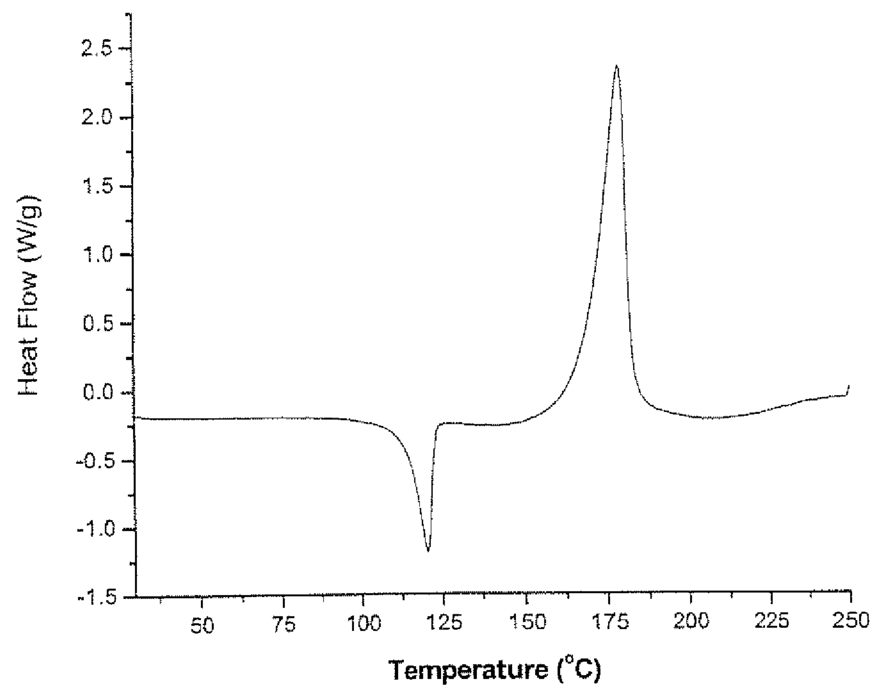
FIG. 1 shows a characteristic differential scanning calorimetry (DSC) trace for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

When tradenames are used herein, applicants intend to independently include the tradename product and the active pharmaceutical ingredient(s) of the tradename product.

Salts of Ethyl N—[(S)({[(2R,5R)-5-(6-amino-9H-purin-9-yl)-4-fluoro-2,5-dihydrofuran-2-yl]oxy}methyl)phenoxyphoshinoyl]-L-alaninate In one aspect, the present invention provides citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

The citrate salt is shown in Formula I:

I

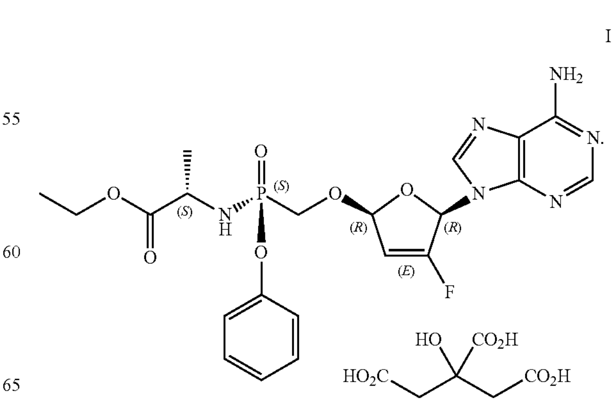

The succinate salt is shown in Formula II:

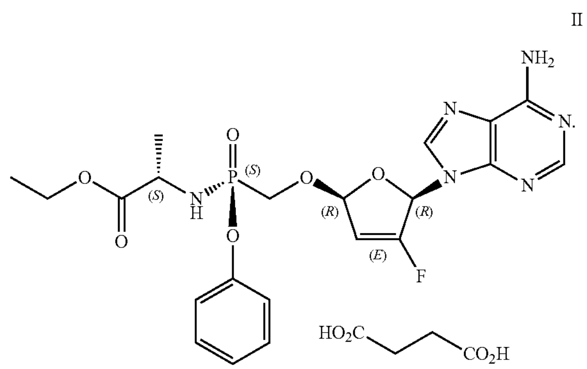

The malonate salt is shown in Formula III:

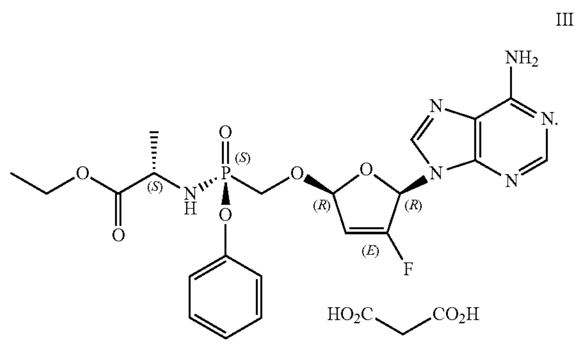

A method for synthesizing Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is described in Example I herein. Methods for making the malonate, succinate and citrate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate are described in Examples 3, 4 and 5, respectively, herein. Some physical properties of the foregoing salts are described in Example 6 herein and demonstrate, for example, that each of these salts is physically stable when stored at 40° C. and a relative humidity of 75%.

The citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate are useful, for example, for inhibiting the replication of 1-HIV in vitro and in vivo. In this regard, as explained more fully in Example 8 herein, Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a prodrug that is metabolized in the human body to yield a parent compound which, in turn, is phosphorylated within the body to produce the active metabolite that inhibits HIV replication. Example 8 herein shows that Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate causes a greater accumulation of the active metabolite in white blood cells, which are the cells that harbor the HIV virus, than does the parent compound. Further, Example 9 herein presents in vitro data showing that Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a more potent anti-HIV drug than the parent compound as assessed in an in vitro assay. Additionally, Example 10 herein provides data showing that a tablet containing the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate provides this drug to the bloodstream of Beagle dogs with similar pharmacokinetics to a liquid preparation of the drug administered orally. Thus, the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a physically and chemically stable composition of matter that can be administered orally to a living subject, to provide a therapeutically effective amount of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, which is a more effective anti-HIV agent than the parent compound.

Pharmaceutical Compositions

In another aspect, the present invention provides pharmaceutical compositions, also referred to as pharmaceutical formulations that include a therapeutically effective amount of one or more salts of the invention, and a pharmaceutically acceptable carrier or excipient.

While it is possible for the salts of the invention to be administered alone, it is typically preferable to administer them as pharmaceutical compositions. The pharmaceutical compositions of the invention are formulated with conventional carriers and excipients, which are selected in accord with ordinary practice. The carrier(s) must be "acceptable" in the sense of being compatible with the other ingredients of the formulation and physiologically innocuous to the recipient thereof. Tablets contain such components as excipients, glidants, fillers, binders and the like. Aqueous formulations are prepared in sterile form, and when intended for delivery by other than oral administration they are generally isotonic. All formulations optionally contain excipients such as those set forth in the *Handbook of Pharmaceutical Excipients* (R. C. Rowe et al., Pharmaceutical Press, $5^{th}$ ed., 2006). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

The formulations may conveniently be presented in unit dosage form (e.g., tablet) and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of salts of the invention contain the active materials in admixture with excipients suitable for the manufacture of aqueous suspensions. Such excipients can include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending, for example, upon the particular mode of administration. For example, a time-release formulation intended for oral administration to humans may contain approximately 1 to 1000 mg of active material compounded with an appropriate and convenient amount of carrier material which may vary from about 5 to about 95% of the total composition (weight:weight).

Formulations suitable for administration to the eye include eye drops wherein the active ingredient is dissolved or suspended in a suitable carrier, especially an aqueous solvent for the active ingredient.

Formulations suitable for topical administration in the mouth include lozenges comprising the active ingredient in a flavored basis, such as sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments of microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HIV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose or an appropriate fraction thereof, of the active ingredient. Thus, for example, a daily dose of a salt of the present invention can be provided in a single tablet, or in multiple tablets (e.g., two or three tablets).

It should be understood that in addition to the ingredients particularly mentioned above the formulations of this invention may include other agents conventional in the art having regard to the type of formulation in question, for example those suitable for oral administration may include flavoring agents.

Pharmaceutical formulations that are also within the scope of the invention provide controlled release of the active ingredient to allow less frequent dosing or to improve the pharmacokinetic or toxicity profile of the active ingredient. Accordingly, the invention also provides pharmaceutical compositions comprising one or more salts of the invention formulated for sustained or controlled release.

An effective dose of a salt of the present invention depends, for example, on whether the salt is being used prophylactically (typically a lower dose is required compared to therapeutic use of the same salt), the method of delivery, and the pharmaceutical formulation, and will be determined by the clinician using conventional dose escalation studies. An effective dose can be expected to be from about 0.0001 mg/kg body weight per day to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily dose for an adult human of approximately 70 kg body weight will typically range from 1 mg to 1000 rug, preferably between 5 mg and 500 mg, and may take the form of single or multiple doses. By way of example, the dose of a salt of the present invention in a unit dose formulation to be administered once per day may be from 1 mg to 100 mg, such as from 30 mg to 60 mg, such as a 30 mg daily dose or a 60 mg daily dose.

Combination Therapy

Each of the citrate, succinate and malonate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate may be employed in combination with other therapeutic agents for the treatment or prophylaxis of AIDS and/or one or more other diseases present in a human subject suffering from AIDS (e.g., bacterial and/or fungal infections, other viral infections such as hepatitis B or hepatitis C, or cancers such as Kaposi's sarcoma). The additional therapeutic agent(s) may be coformulated with one or more salts of the invention (e.g., coformulated in a tablet).

Examples of such additional therapeutic agents include agents that are effective for the treatment or prophylaxis of viral, parasitic or bacterial infections, or associated conditions, or for treatment of tumors or related conditions, include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrotlaymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside valerate; cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI); acyclic nucleosides such as acyclovir, penciclovir, famciciovir, ganciclovir, HPMPC, PMEA, PMEG, PMPA, PMPDAP, FPMPA, HPMPA, HPMPDAP, (2R,5R)-9->tetrahydro-5-(phosphonomethoxy)-2-furanyladenine, (2R,5R)-1->tetrahydro-5-(phosphonomethoxy)-2-furanylthymine; other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate); antibacterial agents including bactericidal fluoroquinolones (ciprofloxacin, pefloxacin and the like); aminoglycoside bactericidal antibiotics (streptomycin, gentamicin, amicacin and the like); β-lactamase inhibitors (cephalosporins, penicillins and the like); other antibacterials including tetracycline, isoniazid, rifampin, cefoperazone, claithromycin and azithromycin, antiparasite or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin; renal excretion inhibitors such as probenicid; nucleoside transport inhibitors such as dipyridamole, dilazep and nitrobenzylthioinosine, immunomodulators such as FK506, cyclosporin A, thymosin α-1; cytokines including TNF and TGF-β; interferons including IFN-α, IFN-β, and IFN-γ; interleukins including various interleukins, macrophage/granulocyte colony stimulating factors including GM-CSF, G-CSr, M-CSF, cytokine antagonists including anti-TNF antibodies, anti-interleukin antibodies, soluble interleukin receptors, protein kinase C inhibitors and the like.

Examples of suitable active therapeutic agents or ingredients which can be combined with the salts of the invention, and which have activity against HIV, include 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG 1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPG-963, MIV-1.50, and TMC-120, TMC-278 efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, tenofovir, tenofovir disoproxil fumamte+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 1.0) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626. PSI-6130 (R1656), HIV-796, BILB 1941, MK-0608, NM-107, 87128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., 1DN-6556, ME 3738, MitoQ, and LB-84451, 18) non-nucleoside inhibitors of HIV, e.g., benzimidazole derivatives, benzo-1,2,4-thiadiazine derivatives, and phenylalanine derivatives, 19) other drugs for treating HIV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, G1-5005, ANA-975 (isatoribine), NTL-6865, ANA 971, NOV-205, tarvacin, EHC-18, and NIM811, 19) pharmacokinetic enhancers, e.g., BAS-100 and SPI452, 20) RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Again by way of example, the following list discloses exemplary HIV antivirals, with their corresponding U.S. Patent numbers that can be combined with the salts of the present invention.

Exemplary HIV Antivirals and Patent Numbers

Ziagen (Abacavir sulfate, U.S. Pat. No. 5,034,394)
Epzicom (Abacavir sulfate/lamivudine, U.S. Pat. No. 5,034,394)
Hepsera (Adefovir dipivoxil, U.S. Pat. No. 4,724,233)
Agenerase (Amprenavir, U.S. Pat. No. 5,646,180)
Reyataz (Atazanavir sulfate, U.S. Pat. No. 5,849,911)
Rescriptor (Delavirdine mesilate, U.S. Pat. No. 5,563,142)
Hivid (Dideoxycytidine; Zalcitabine, U.S. Pat. No. 5,028,595)
Videx (Dideoxyinosine; Didanosine, U.S. Pat. No. 4,861,759)
Sustiva (Efavirenz, U.S. Pat. No. 5,519,021)
Emtriva (Eintricitabine, U.S. Pat. No. 6,642,245)
Lexiva (Fosamprenavir calcium, U.S. Pat. No. 6,436,989)
Virudin; Thaptem Foscavir (Foscarnet sodium, U.S. Pat. No. 6,476,009)
Crixivan (Indinavir sulfate, U.S. Pat. No. 5,413,999)
Epivir (Lamivudine, U.S. Pat. No. 5,047,407)
Combivir (Lamivudine/Zidovudine, U.S. Pat. No. 4,724,232)
Aluviran (Lopinavir)
Kaletra (Lopinavir/ritonavir, U.S. Pat. No. 5,541,206)
Viracept (Nelfinavir mesilate, U.S. Pat. No. 5,484,926)
Viramune (Nevirapine, U.S. Pat. No. 5,366,972)
Norvir (Ritonavir, U.S. Pat. No. 5,541.206)
Invirase; Fortovase (Saquinavir mesilate, U.S. Pat. No. 5,196,438)
Zerit (Stavudine, U.S. Pat. No. 4,978,655)
Truvada (Tenofovir disoproxil fumarate/erntricitabine, U.S. Pat. No. 5,210,085)
Aptivus (Tipranavir)
Retrovir (Zidovudine; Azidothyrnidine, U.S. Pat. No. 4,724,232)

Methods of Inhibition of HIV

In a further aspect, the present invention provides methods of treating Acquired Immune Deficiency Syndrome (AIDS), wherein each method includes the step of administering to a human being suffering from AIDS a therapeutically effective amount of a salt of the invention, or a hydrate of a salt of the invention. Treatment of AIDS includes the amelioration of at least one symptom of AIDS, and/or slowing or preventing the progression of the disease. Typically the therapeutically effective amount of the salt is administered to a human being in the form of a pharmaceutical composition, as described under the heading "Pharmaceutical Compositions". Typically, the pharmaceutical composition is administered orally, for example in the form of a tablet. Examples of therapeutically effective daily doses of one or more salts of the invention, or hydrates thereof, are from 1 mg to 100 mg, such as from 10 mg to 30 mg. The salts of the invention can be administered daily, for example in the form of one or more tablets that include an amount of salt that provides an effective amount, such as 10 mg or 30 mg or 60 mg, of the free base when the salt dissociates in an aqueous medium within the human body.

Routes of Administration

One or more salts of the invention are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with, for example, the condition of the recipient. An advantage of the salts of the present invention is that they are orally bioavailable and can be dosed orally.

Examples and Exemplary Embodiments

See also WO 2006/110157, the disclosure of which is herein incorporated by reference in its entirety, particularly, pages 167-174.

Example 1

Synthesis of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate (2)

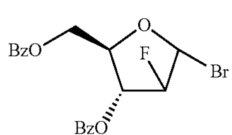

2-deoxy-2-fluoro-3,5-di-O-benzoyl-α-D-arabinofuranosylbromide (2)

Compound (2) was synthesized according to the synthetic schemes disclosed in Tann et. al., JOC, 1985, Vol. 50 pg. 3644 and Howell et. al., JOC, 1988, Vol. 53, pg. 85.

To a solution of 1.3.5-tri-O-benzoyl-2-deoxy-2-fluoro-α-D-arabinofuranose (1) (120 g, 258 mmol), commercially available from Davos or CMS chemicals, in $CH_2Cl_2$ (1 L) was added 33% HBr/Acetic acid (80 mL). The mixture was stirred at room temperature for 16 h, cooled with ice-water, and slowly neutralized over 1-2 h with $NaHCO_3$ (150 g/1.5 L solution).

The $CH_2Cl_2$ phase was separated and concentrated under reduced pressure. The residue was dissolved in ethyl acetate and washed with $NaHCO_3$ until no acid was present. The organic phase was dried over $MgSO_4$, filtered and concentrated under reduced pressure to give product 2 as a yellow oil (~115 g).

(3)

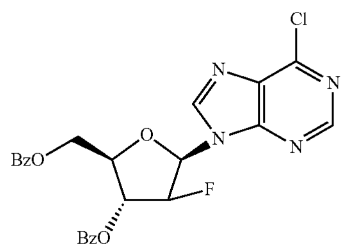

2-deoxy-2-fluoro-3,5-di-O-benzoyl-β-D-arabinofuranosyl-9H-6-chloropurine (3)

Compound (3) was synthesized according to the synthetic schemes disclosed in Ma et. al., Med. Chem., 1997, Vol. 40, pg. 2750; Marquez et. al., 3. Med. Chem., 1990, Vol. 33, pg. 978; Hildebrand et. al., J. Org. Chem., 1992, Vol. 57, pg. 1808 and Kazimierczuk et. al., JACS, 1984, Vol. 106, pg. 6379.

To a suspension of NaH (14 g, 60%) in Acetonitrile (900 mL), 6-chloropurine (52.6 g) was added in 3 portions. The mixture was stirred at room temperature for 1.5 h. A solution of 2 (258 mmol) in Acetonitrile (300 mL) was added dropwise. The resulting mixture was stirred at room temperature for 16 h. The reaction was quenched with Acetic acid (3.5 filtered and concentrated under reduced pressure. The residue was partitioned between $CH_2Cl_2$ and water. The organic phase was dried over $MgSO_4$, filtered and concentrated. The residue was treated with $CH_2Cl_2$ and then EtOH (~1:2 overall) to precipitate out the desired product 3 as a yellowish solid (83 g, 65% from 1).

(4)

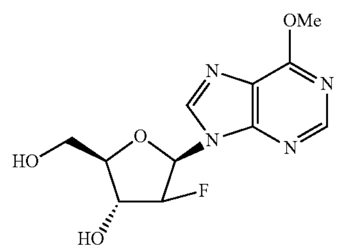

2-deoxy-2-fluoro-β-D-arabinofuranosyl-6-methoxyadenine (4)

To a suspension of 3 (83 g, 167 mmol) in Methanol (1 L) at 0° C., NaOMe (25% wt, 76 mL) was added. The mixture was stirred at room temperature for 2 h, and then quenched with Acetic acid (~11 mL, pH=7). The mixture was concentrated under reduced pressure and the resultant residue partitioned between hexane and water (approximately 500 mL hexane and 300 mL water). The aqueous layer was separated and the organic layer mixed with water once again (approximately 300 mL). The water fractions were combined and concentrated under reduced pressure to ~100 mL. The product, 4, precipitated out and was collected by filtration (42 g, 88%).

(5)

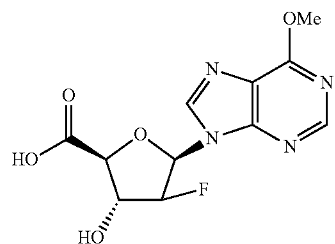

2-deoxy-2-fluoro-5-carboxy-β-D-arabinofuranosyl-6-methoxyadenine (5)

Compound (5) was synthesized according to the synthetic schemes disclosed in Moss et. al., J. Chem. Soc. 1963, pg. 1149.

A mixture of Pt/C (10%, 15 g (20-30% mol equiv.) as a water slurry) and $NaHCO_2$ (1.5 g, 17.94 mmol) in $H_2O$ (500 mL) was stirred at 65° C. under $H_2$ for 0.5 h. The reaction mixture was then allowed to cool, placed under a vacuum and flushed with $N_2$ several times to completely remove all $H_2$. Compound 4 (5.1 g, 17.94 mmol) was then added at room temperature. The reaction mixture was stirred at 65° C., under $O_2$ (balloon) until the reaction was complete by LC-MS (typically 24-72 h). The mixture was cooled to room temperature and filtered. The Pt/C was washed with $H_2O$ extensively. The combined filtrates were concentrated to ~30 mL, and acidified (pH 4) by the addition of HCl (4N) at 0° C. A black solid precipitated out which was collected by filtration. The crude product was dissolved in a minimum amount of Methanol and filtered through a pad of silica gel (eluting with Methanol). The filtrate was concentrated and crystallized from water to give compound 5 (2.5 g) as an off-white solid.

(6)

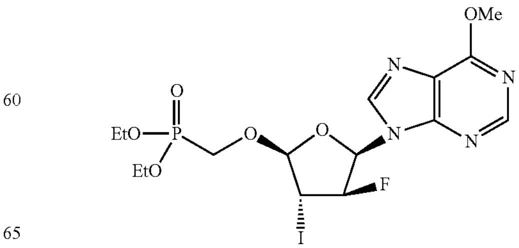

(2'R, 3'S, 4'R, 5'R)-6-Methoxy-9-[tetrahydro 4-iodo-3-fluoro-5-(diethoxyphosphinyl)methoxy-2-furanyl] purine (6)

Compound (6) was synthesized according to the synthetic schemes disclosed in Zemlicka et. al., J. Amer. Chem., Soc., 1972, Vol. 94, pg. 3213.

To a solution of 5 (22 g, 73.77 mmol) in DMF (400 mL), DMF dineopentyl acetal 050 mL, 538 mmol) and methanesulfonic acid (9.5 mL, 146.6 mmol) were added. The reaction mixture was stirred at 80-93° C. (internal temperature) for 30 min, then cooled to room temperature and concentrated under reduced pressure. The residue was partitioned between ethyl acetate and water. The organic phase was separated and washed with $NaHCO_3$ followed by brine, dried over $MgSO_4$, filtered and concentrated under reduced pressure. The residue and diethyl (hydroxymethyl)phosphonate (33 mL, 225 mmol) were dissolved in $CH_2Cl_2$ (250 mL) and cooled down to −40° C. A solution of iodine monobromide (30.5 g, 1.1 mol) in $CH_2Cl_2$ (100 mL) was added dropwise. The mixture was stirred at −20 to −5° C. for 6 h. The reaction was then quenched with $NaHCO_3$ and $Na_2S_2O_3$. The organic phase was separated and the water phase was extracted with $CH_2Cl_2$. The combined organic phases were washed with brine, dried over $MgSO_4$, filtered and concentrated under reduced pressure. The residue was purified by silica gel chromatography to give product 6 (6 g, 15.3%).

Alternative Procedure for the Preparation of 6

A solution of 5 (2.0 g, 6.7 mmol) in THF (45 mL) was treated with triphenyl phosphine (2.3 g, 8.7 mmol) under ND. Diisopropyl azodicarboxylate (1.8 g, 8.7 mmol) was added slowly. The resultant mixture was stirred at room temperature for 1 h and then concentrated under reduced pressure to dryness. The residue was dissolved in $CH_2Cl_2$ (20 ml), and then treated with diethyl(hydroxymethyl)phosphonate (4.5 g, 27 mmol). The mixture was cooled to −60° C. and then a cold solution of iodine monobromide 2 g, 9.6 mmol) in $CH_2Cl_2$ (10 ml) was added. The reaction mixture was warmed to −10° C. and then kept at −10° C. for 1 h. The reaction mixture was diluted with $CH_2Cl_2$, washed with saturated aqueous $NaHCO_3$, and then with aqueous sodium thiosulfate. The organic phase was separated, dried over $MgSO_4$, and concentrated under reduced pressure to dryness. The reaction mixture was purified by silica gel chromatography (eluting with 25% ethyl acetate in $CH_2Cl_2$, then switching to 3% methanol in $CH_2Cl_2$) to afford product 6 (0.9 g, 33%).

(7)

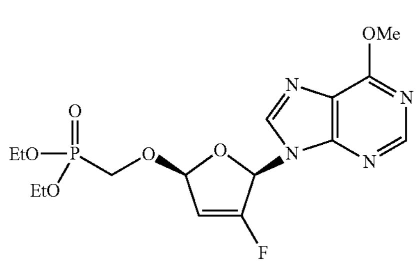

(2'R, 5'R)-6-Methoxy-9-[3-fluoro-2,5-dihydro-5-(diethoxyphosphinyl)methoxy-2-furanyl]purine (7)

To a solution of compound 6 (6 g, 11.3 mmol) in acetic acid (2.5 mL) and methanol (50 mL), NaClO (10-13%) (50 mL) was added dropwise. The reaction mixture was then stirred for 0.5 h and concentrated under reduced pressure. The residue was treated with ethyl acetate and then filtered to remove solids. The filtrate was concentrated and the residue was purified by silica gel chromatography to give product 7 (4 g, 88%).

(8)

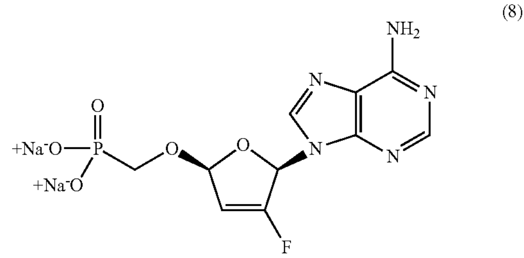

(2'R, 5'R)-9-(3-fluoro-2,5-dihydro-5-phosphonomethoxy-2-furanyl)adenine di sodium salt (8)

A solution of compound 7 (2.3 g, 5.7 mmol) in methanol (6 mL) was mixed with ammonium hydroxide (28-30%) (60 mL). The resultant mixture was stirred at 120° C. for 4 h, cooled, and then concentrated under reduced pressure. The residue was dried under vacuum for 12 h. The residue was dissolved in DMF (40 mL) and bromotrimethylsilane (3.5 mL) was added. The mixture was stirred at room temperature for 16 h, and then concentrated under reduced pressure. The residue was dissolved in aqueous $NaHCO_3$ (2.3 g in 100 ml of water). The solution was evaporated and the residue was purified on C-18 (40 μm) column, eluting with water. The aqueous fractions were freeze dried to give di-sodium salt 8 (1.22 g, 57%).

(9)

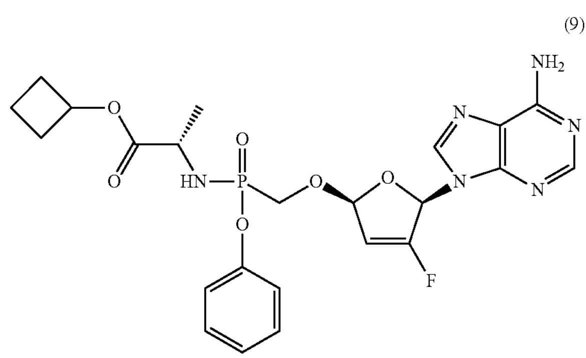 [SMILES: C[C@H](NP(=O)(CO[C@@H]1C=C(F)[C@H](n2cnc3c(N)ncnc32)O1)Oc1ccccc1)C(=O)OC1CCC1]

Example of Monoamidate Preparation (9)

Di sodium salt 8 (25 mg, 0.066 mmol), (S)-Ala-O-cyclobutyl ester hydrochloride (24 mg, 2 eq., 0.133 mmol) and phenol (31 mg, 0.333 mmol) were mixed in anhydrous pyridine (1 mL). Triethylamine (111 μl, 0.799 mmol) was added and the resultant mixture was stirred at 60° C. under nitrogen. In a separate flask, 2'-Aldrithiol (122 mg, 0.466 mmol) and triphenylphosphine (103 mg, 0.466 mmol) were dissolved in anhydrous pyridine (0.5 mL) and the resulting yellow solution was stirred for 15-20 min. The solution was then added to the solution of 8 in one portion. The combined mixture was stirred at 60° C. under nitrogen for 16 h to give a clear yellow to light brown solution. The mixture was then concentrated under reduced pressure. The resultant oil was dissolved in $CH_2Cl_2$ and purified by silica gel chromatography (eluting with a linear gradient of 0 to 5% MeOH in $CH_2Cl_2$) to give an oil. The resulting oil was dissolved in acetonitrile and water and purified by preparative HPLC (linear gradient, 5-95% acetonitrile in water). Pure fractions were combined and freeze-dried to give mono amidate 9 as a white powder.

(10)

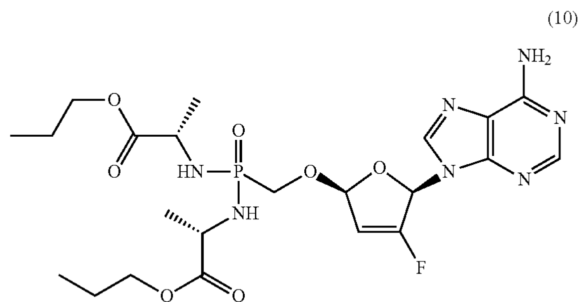 [SMILES: CCCOC(=O)[C@H](C)NP(=O)(CO[C@@H]1C=C(F)[C@H](n2cnc3c(N)ncnc32)O1)N[C@@H](C)C(=O)OCCC]

Example of Bis Amidate Preparation (10)

Di sodium salt 8 (12 mg, 0.032 mmol) and (S)-Ala-O-n-Pr ester hydrochloride (32 mg, 6 eq., (1.192 mmol) were mixed in anhydrous pyridine (1 mL). Triethylamine (53 µL, 0.384 mmol) was added and the resultant mixture was stirred at 60° C. under nitrogen. In a separate flask, 2'-Aldrithiol (59 mg, 0.224 mmol) and triphenylphosphine (49 mg, 0.224 mmol) were dissolved in anhydrous pyridine (0.5 mL) and the resulting yellow solution was stirred for 15-20 min. The solution was then added to the solution of 8 in one portion. The combined mixture was stirred at 60° C. under nitrogen for 16 h to give a clear yellow to light brown solution. The mixture was then concentrated under reduced pressure. The resultant oil was dissolved in $CH_2Cl_2$ and purified by silica gel chromatography (eluting with a linear gradient of 0 to 5% MeOH in $CH_2Cl_2$) to give an oil. The resulting oil was dissolved in acetonitrile and water and purified by preparative HPLC (linear gradient, 5-95% acetonitrile in water). Pure fractions were combined and freeze-dried to give his amidate as a white powder.

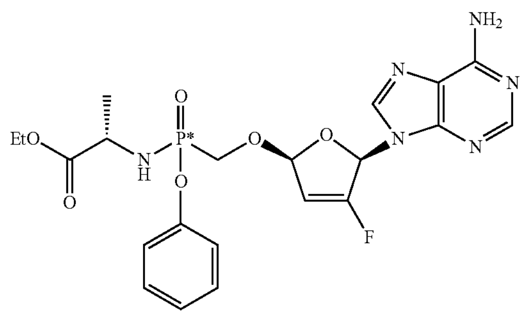

Example of Monoamidate Preparation (11)

Compound 8 (1.5 g, 4 mmol) was mixed with ethyl alanine ester HCl salt (1.23 g, 8 mmol) and phenol (1.88 g, 20 mmol). Anhydrous pyridine (35 mL) was added followed by TEA (6.7 mL, 48 mmol). The mixture was stirred at 60° C. under nitrogen for 15-20 min. 2'-Aldrithiol (7.3 g) was mixed in a separate flask with triphenylphosphine (6.2 g) in anhydrous pyridine (5 mL) and the resultant mixture was stirred for 10-15 min to give a clear light yellow solution. The solution was then added to the above mixture and stirred overnight at 60° C. The mixture was concentrated under reduced pressure to remove pyridine. The resultant residue was dissolved in ethyl acetate and washed with saturated sodium bicarbonate solution (2×) and then with saturated sodium chloride solution. The organic layer was dried over sodium sulfate, filtered and then concentrated under reduced pressure. The resultant oil was dissolved in dichloromethane and loaded onto a dry CombiFlash column, 40 g, eluting with a linear gradient of 0-5% methanol in dichloromethane over 10 min and then 5% methanol in dichloromethane for 7-10 min. Fractions containing the desired product were combined and concentrated under reduced pressure to give a foam. The foam was dissolved in acetonitrile and purified by prep HPLC to give 11 (0.95 g).

Dissolved 11 (950 mg) in small amount of acetonitrile and let stand at room temperature overnight. Collected solid by filtration and washed with small amount of acetonitrile. Filtrate was reduced under vacuum and then loaded onto Chiralpak AS-H column equilibrated in Buffer A, 2% ethanol in acetonitrile. Isomer A, 12, was eluted out with Buffer A at 10 mL/min for 17 mins. After which Buffer B, 50% methanol in acetonitrile, was used to elute isomer B, 13, separately out from the column in 8 mins. Removed all solvent and then separately re-dissolved in acetonitrile and water. Separately freeze-dried the samples (Mass-348 mg). Isomer 12 is shown below (12)

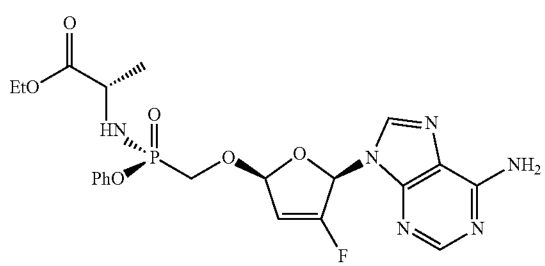

Example 2

Screening Salt Forms of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The following acids were screened to determine whether they formed suitable crystalline salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate: Mineral acids (HX, wherein X=halogen; $H_3PO_4$); organic sulfonie acids ($RSO_3H$, wherein R=Me, Et, Ph, (+)-camphor-10-sulfonic acid; naphthalene-2-sulfonic acid; naphthalene-1,5-disulfonic acid); mono carboxylic acids ($RCO_2H$, wherein R=H, Me, Et, Ph, trans-PhCH=CH, $Cl_2CH$, $PhCONHCH_2$), and dicarboxylic acids (malonic, succinic, fumaric, adipic, oxalic, maleic).

Solids were obtained with three of the foregoing acids when mixed with Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate: trifluoroacetic acid, malonic acid, and succinic acid. Trifluoroacetic acid is not considered to be pharmaceutically acceptable.

Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is an amidate prodrug which undergoes decomposition in protic solvents under acidic or basic conditions. For this reason, acids with potentially nucleophilic moieties were not included in the initial round of screening. Subsequently, citric acid, glycolic acid, (S)-(±)-lactic acid, salicylic acid, (S)-(−)-malic acid, (S)-(+)-mandelic acid and (S)-(+)-glutamic acid were evaluated. Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate unexpectedly formed a stable crystalline salt with citric acid. This was an unexpected result because citric acid includes a hydroxyl group which can act as a nucleophile toward the amidate moiety of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate and potentially undergo a reaction therewith in which a covalent bond is formed between Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate and the hydroxyl group of citric acid with the expulsion of either phenol or alanine ethyl ester.

Example 3

Synthesis of Malonate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was dissolved in warm 2-butanone (15 parts), and malonic acid (0.26 parts) was added to form a solution with agitation. Heptane (5 parts) was added to the solution which was slowly cooled to about 5° C., collected and rinsed with cold 2-butanone/heptane. The resulting malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was thereby produced with a yield of about 80%.

The NMR spectrum of the malonate salt had the following characteristics: $^{1}$H NMR (400 MHz, CHLOROFORM-d) ppm=8.27 (s, 1H), 8.26 (s, 1H), 7.32-7.20 (m, 3H), 7.15 (d, J=7.8 Hz, 2H), 6.78 (m, 1H), 5.88 (hr. s, 1H), 5.78 (s, 1H), 4.17 (m, 2H), 4.15-4.07 (m, 3H), 3.85 (dd, J=8.0, 8.0, 1H), 3.38 (s, 2H), 1.31 (d, J=7.0 Hz, 3H), 1.23 (t, J=7.0 Hz, 3H)

$^{31}$P NMR (162 MHz, CHLOROFORM-d) ppm=20.64 (s)

$^{19}$F NMR (376 MHz, ACETONITRILE-d3) ppm=−135.19 (s)

Example 4

Synthesis of Succinate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was dissolved in warm 2-butanone (15 parts), and succinic acid (0.28 parts) was added to form a solution with agitation. The solution was slowly cooled to about 5° C., collected, and rinsed with cold 2-butanone, thereby yielding the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate at a yield of 80%.

The NMR spectrum of the succinate salt had the following characteristics: $^{1}$H NMR (400 MHz, ACETONITRILE-d3) ppm=8.26 (s, 1H), 8.15 (s, 1H), 7.29 (dd. J=7.6, 7.6 Hz, 2H), 7.16 (d, J=7.6 Hz, 1H), 7.12 (d, J=8.0 Hz, 2H), 6.78 (m, 1H), 6.17 (br s, 1H), 5.89 (m, 2H), 4.12-3.95 (overlapped multiplets, 6H), 2.53 (s, 4H), 1.24 (d, J=6.8, 3 H), 1.18 (t, J=7.2, 3 H).

$^{31}$P NMR (162 MHz, Acetonitrile-d3) ppm=21.60 (s)

$^{19}$F NMR (376 MHz, Acetonitrile-d3) ppm=−135.19 (s)

Example 5

Synthesis of Citrate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The free base form of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate (about 30 g) was dissolved in hot acetonitrile (16 parts) and citric acid (0.38 parts) were added with agitation. The resulting solution was slowly cooled to about 5° C., collected and rinsed with cold acetonitrile, and dried, thereby affording the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate with a yield of about 84%.

The NMR spectrum of the citrate salt had the following characteristics: $^{1}$H NMR (400 MHz, DMSO-d6) ppm=8.20 (s, 2H), 7.45 (2H, br s), 7.29 (dd, J=7.6, 7.6 Hz, 2H), 7.13 (dd, J=7.2 Hz, J=7.2 Hz 1H), 7.12 (dd, J=8.0 Hz, J=8.0 Hz 2H), 6.86 (d, J=2.4 Hz, 1H), 6.14 (s, 1H), 5.97 (d, J=3.6 Hz, 1H), 5.78 (dd, J=12.2, 10.4 Hz, 1H), 4.05 (m, 1H), 4.02 (m, 2H), 3.98 (m, 1H), 3.89 (m, 1H), 2.76 (d, J=15.6 Hz, 2H), 2.66 (d, J=15.6 Hz, 2H), 1.16 (d, J=7.2 Hz, 1H).

$^{31}$P NMR (162 MHz, DMSO-d6) ppm=22.29 (s)

$^{19}$F NMR (376 MHz, ACETONITRILE-d3) ppm=−133.88 (s)

HRMS: m/z: 507.1561; Calcd for $C_{21}H_{24}FN_6O_6P$, 507.1557.

Anal. Calcd for $C_{21}H_{24}FN_6O_6P$, C, 46.42; H, 4.62; N, 12.03; P, 4.43; F, 2.72. Found: C, 45.83; H, 4.74; N, 11.81; P, 4.45; F, 2.80.

Example 6

Physicochemical Properties of Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Representative batches of the malonate, succinate, and citrate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate were prepared. The melting points of these salts were determined and serve as a rough measure of stability with a higher melting point indicating a higher level of stability. As shown in Table 1, the citrate salt had the highest melting point. Additionally, the heat of fusion ($\Delta H_{(fusion)}$) of each of the three salts is shown in Table 1. The citrate salt had the highest heat of fusion indicating a higher degree of solid-state crystallinity than the other two salts.

TABLE 1

Melting Temperatures and Heat of Fusion of Succinate, Malonate and Citrate Salts of Ethyl N-[(S)({[(2R,5R)-5-(6-amino-9H-purin-9-yl)-4-fluoro-2,5-dihydrofuran-2-yl]oxy}methyl)phenoxyphosphinoyl]-L-alaninate

| Salt | Molecular Weight | $\Delta H_{(fusion)}$ J/g | $T_m$ (° C.) |
|---|---|---|---|
| Succinate Salt | 624.52 | 58.85 | 138.06 |
| Malonate Salt | 610.49 | 66.10 | 120.13 |
| Citrate Salt | 698.56 | 127.59 | 149.76 |

The free base foam of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is amorphous, hygroscopic and chemically unstable when stored under open condition at 40° C. and 75% relative humidity (RH). As shown in Table 2, the corresponding succinate, malonate and citrate salts were not hygroscopic at room temperature when exposed to a relative humidity of 92% for several days,

TABLE 2

Solid State Hygroscopicity of Salt Forms of Ethyl N-[(S)({[(2R,5R)-5-(6-amino-9H-purin-9-yl)-4-fluoro-2,5-dihydrofuran-2-yl]oxy}methyl)phenoxyphosphinoyl]-L-alaninate at Room Temperature

| Salt | Time (days) | 20-25° C./ 92% RH |
|---|---|---|
| Succinate Salt | 0 | 0.01 |
| | 13 | 0.010 |
| Malonate Salt | 0 | 0.02 |
| | 13 | 0.12 |
| Citrate Salt | 0 | 0.01 |
| | 25 | 0.02 |

The solid-state chemical stability of the free base, succinate, malonate and citrate salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate were examined under open conditions at 40° C. and 75% relative humidity. As shown in Table 3, the citrate salt displayed superior chemical stability compared to the succinate and malonate salts.

TABLE 3

Solid State Stability of Free Base form of Ethyl N-[(S)({[(2R,5R)-5-(6-amino-9H-purin-9-yl)-4-fluoro-2,5-dihydrofuran-2-yl]oxy}methyl)phenoxyphosphinoyl]-L-alaninate, and the corresponding Succinate, Citrate and Malonate Salts at 40° C./75% Relative Humidity Under Open Conditions

| Form | Time (days) | Free Base (%) | Other Impurities (%) |
|---|---|---|---|
| Free Base | 0 | 99.01 | 0.99 |
| | 7 | 82.95 | 17.05 |
| | 14 | 66.89 | 33.11 |
| | 22 | 55.90 | 44.10 |
| Succinate Salt | 0 | 98.95 | 1.05 |
| | 9 | 95.15 | 4.85 |
| | 16 | 92.47 | 7.53 |
| | 22 | 90.43 | 9.57 |
| | 30 | 85.92 | 14.08 |
| Malonate Salt | 0 | 97.82 | 2.18 |
| | 9 | 94.66 | 5.34 |
| | 16 | 92.97 | 7.03 |
| | 22 | 93.48 | 6.52 |
| | 30 | 85.84 | 14.16 |
| Citrate Salt | 0 | 98.00 | 2.00 |
| | 4 | 97.27 | 2.73 |
| | 12 | 97.20 | 2.80 |
| | 17 | 95.86 | 4.14 |
| | 27 | 94.59 | 5.41 |

Example 7

Composition of Tablets Providing Equivalent of 10 mg and 30 mg of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Free Base The citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate was formulated into 10 mg and 30 mg tablets using the roller compaction process. The active ingredient, lactose anhydrous, microcrystalline cellulose and crosearmellose sodium were first blended, the mixture was then lubricated with one third of the total amount of magnesium stearate, then roller compacted, followed by milling. The resulting granules were lubricated with the remaining amount of magnesium stearate and pressed into tablets.

Table 4 shows the compositon of tablets that include the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate, and that provide either 10 mg or 30 mg of the free base form of the compound when the citrate salt dissociates in an aqueous medium.

TABLE 4

| Components | % w/w | Tablet Unit Formula (mg/unit) 10 mg | 30 mg | Compendial Reference | Function |
|---|---|---|---|---|---|
| Citrate Salt | 13.79[a] | 13.79[a,b] | 41.37[a,c] | HSE | Active Ingredient |
| Lactose Anhydrous[d] | 66.00 | 66.00 | 198.00 | NF | Diluent/ Filler |
| Microcrystalline Cellulose | 15.21 | 15.21 | 45.63 | NF | Binder/ Filler |
| Croscarmellose Sodium | 3.50 | 3.50 | 10.50 | NF | Disintegrant |
| Magnesium Stearate | 1.50 | 1.50 | 4.50 | NF | Lubricant |
| Total | 100.00 | 100.00 | 300.00 | | |

[a]Equivalent to 10% 2/2 of free base form of compound. Actual drug substance weight will be adjusted to account for drug substance purity.
[b]Equivalent to 10 mg of free base form of compound.
[c]Equivalent to 30 mg of free base form of compound.
[d]The adjusted drug substance quantity will be subtracted from the quantity of anhydrous lactose.
[e]The abbreviation NF means national formulary, and the abbreviation HSE means House Compendial Reference which is the internal standard used at Gilead Sciences.

Example 8

Comparison of Lymphocyte Loading of Active Metabolite After Administration to Lymphocytes of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate (Prodrug) or Parent Compound Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate is a prodrug that is hydrolyzed in the human body to yield a hydrolysis product that is hereinafter referred to as "the parent compound". The parent compound is phosphorylated within the human body to produce a biologically active phosphorylated product (hereinafter "the active metabolite") which inhibits the activity of reverse transcriptase enzyme.

To characterize the intracellular metabolism of the prodrug and parent compound, lymphocyte cells were treated with either 1 μM prodrug or 100 μM parent compound for 2, 6, and 24 hours. Peripheral blood mononuclear cells (PBMCs) were isolated from human buffy coats (Stanford Blood Bank, Palo Alto, Calif.) using centrifugation in Ficoll Paque Plus (GE Healthcare, Piscataway, N.J.) according to manufacturer's procedure. PBMCs isolated from 3 to 4 independent donors were maintained in RPMI-1640 media with 20% fetal bovine serum and antibiotics (quiescent state) or were activated in the presence of interleukin 2 (20 units/mL, Roche Biochemicals, Indianapolis, Ind.) and phytohemagglutinin PHA-P (1 μg/mL, Sigma) for 3 to 4 days before the initiation of experiments.

Human transformed CCRF-CEM T-cells were obtained from The American Type Culture Collection (Manassas, Va.) and cultured in RPMI-1640 medium supplemented with 10% PBS and antibiotics. An aliquot of cells ($2-3\times10^6$ cells) was collected at each time point, counted, pelleted by centrifugation, resuspended in 0.5 mL of the original treatment media and layered onto 0.5 mL of Nyosil M25 oil. The samples were spun in a microcentrifuge for 20 seconds at the maximum speed (approximately 800×g). The top layer of media was removed and the oil layer was washed twice with 0.8 mL phosphate-buffered saline. Washing buffer and the oil layer were carefully removed, the cell pellet was resuspended in 0.5 mL 70% methanol and incubated overnight at −70° C. to facilitate cell lysis. Cell lysates were centrifuged, supernatants collected, dried by vacuum and resuspended in 10 μL tetrabutyl ammonium acetate containing the diphosphate of [5-(6-Amino-purin-9-yl)-2,5-dihydro-furan-2-yloxymethyl]-phosphonic acid (the non-fluorinated analog of the active metabolite) as an internal standard.

Transient ion-pairing high-performance liquid chromatography coupled to positive ion electrospray tandem mass spectrometery (LC/MS/MS) was used to quantitate intracellular nucleotides. Methods were adapted from those described for the acyclic phosphonate nucleotide analog adefovir, its phosphorylated metabolites and natural nucleotides (Vela, J. E. et al. Simultaneous quantitation of the nucleotide analog adefovir, its phosphorylated anabolites and 2'-deoxyadenosine triphosphate by ion-pairing LC/MS/MS. Journal of Chromatography B Anal. Technol. Biomed. Life Sci., vol. 848, 2007, pp 335-343). Standard curves and quality control samples were generated for all analytes using extracts from untreated cells. Seven point standard curves generally ranged from 0.03 to 20 μmol/million cells and had linearity in excess of $r^2$ equal to 0.99 for all analytes. The lower limits of quantitations for all analytes ranged from 0.05 to 0.1 pmol/million cells. Low and high concentration quality control samples (typically 0.2 and 10 pmol/million cells, respectively) were run with each analyte at the beginning and end of each analytical run to assure accuracy and precision within 20%.

The parent compound was incubated at a 100-fold higher concentration (100 μM) than the prodrug (1 μM) to facilitate accurate analysis of the much lower intracellular accumulation of metabolites observed following incubation of lymphocytes with the parent compound. As shown in Table 5, the prodrug induced 76-, 290- and 140-fold increased levels of the active metabolite relative to the parent compound following incubation with CEM-CCRF, quiescent PBMCs and activated PBMCs, respectively. Active metabolite levels were normalized based on extracellular concentration following incubations with 1 μM prodrug or with 100 μM parent compound.

TABLE 5

| | Dose Normalized Active Metabolite Concentration ((pmol/million)/1 μM media concentration) | | |
|---|---|---|---|
| | CEM-CCRF | Quiscent PBMC | Activated PBMC |
| Parent Compound | 0.087 ± 0.014 | 0.012 ± 0.004 | 0.045 ± 0.004 |
| Prodrug | 6.57 ± 1.00 | 3.52 ± 0.96 | 6.45 ± 1.64 |

Values represent the mean ± standard deviation of three independent experiments performed in duplicate Example 9

Comparison of Anti-HIV Activity of the Prodrug and the Parent Compound

The terms "prodrug" and "parent compound" have the meanings set forth in Example 8.

MT-2 cells were maintained in RPMI-1640 medium supplemented with antibiotics and 10% fetal bovine serum (FBS), MT-2 cells were infected with HIV-1 IIIB at a multiplicity of infection (moi) of 0.01 and added to 96-well plates with serial dilutions of tested compounds at a density of 20,000 cells/well. After a 5-day incubation, the virus-induced cytopathic effect was determined using a CellTiter-Glo™ cell viability assay (Prometa, Madison, Wis.) and expressed as a percentage of the signal from samples with fully suppressed virus replication after the subtraction of signal from the untreated control. The concentration of each drug that inhibited the virus-induced cytopathic effect by 50% ($EC_{50}$) was determined by non-linear regression. Activity against NRTI-resistant mutants was determined in parallel with wild-type control virus and fold change in $EC_{50}$ was calculated.

Human peripheral blood mononuclear cells (PBMC) were isolated from donor huffy coats using centrifugation in Ficoll Paque Plus and activated for 4-5 days in RPMI-1640 medium with 20% FBS, antibiotics, interleukin-2 (20 units/mL) and phytohemagglutinine PHA-P (1 μg/mL). Activated PBMC were infected with HIV-1 BaL for 3 hours, washed, seeded into 96-well plates (250,000 cells/well) and incubated with serial dilutions of tested compounds for 5 days, at which point cell supernatants were collected and virus production was determined using commercial HIV-1 p24 ELISA (Beckman Coulter, Miami, Fla.). The concentration of each drug inhibiting the p24 antigen production by 50% (EC50) was determined by regression analysis.

The effect of the addition of pro-moieties on the anti-HIV activity was assessed in MT-2 and stimulated PBMC infected with HIV-1. As shown in Table 6, the prodrug was 71- and 2,300-fold more potent than the parent compound in MT-2 and activated PBMC, respectively.

TABLE 6

Anti-HIV-1 activity of the prodrug and the parent compound in a lymphoid derived cell line and primary lymphoid cells.

| | $EC_{50}$ (μM) | |
|---|---|---|
| | MT-2 | PBMC |
| Parent Compound | 10.6 ± 2.4 | 8.5 ± 7.7 |
| Prodrug | 0.15 ± 0.04 | 0.0037 ± 0.0001 |

Values represent the mean ± standard deviation from at least two dependent experiments performed in triplicate.

Example 10

Oral Bioavailability of the Citrate Salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate After Administration in Tablet Form to Beagle Dogs The dosing group consisted of 3 non-näive male beagle dogs. The animals were fasted overnight prior to dose administration and up to 4 hr after dosing. Dogs were administered a single tablet containing 41.38 mg of the citrate salt of the prodrug (providing 30 rag of the prodrug per tablet). The tablet consisted of 13.79% of the citrate salt of the prodrug, 66% anhydrous lactose, 15.21% microcrystalline cellulose, 3.5% sodium croscamellose and 1.5% magnesium stearate on a weight per weight basis. Plasma samples were obtained prior to dosing (0 hr) and at 0.083, 0.25, 0.50, 1.0, 2.0, 4.0, 8.0, 12, 24 hr. The blood samples were collected into Vacutainer™ tubes containing EDTA-$K_3$. The blood samples were centrifuged at 4° C. to separate plasma. An aliquot of 100 μl of each plasma sample was first diluted with 300 μl 80% acetonitrile/water containing 200 nM internal standard. Following centrifugation of the protein precipitate, 100 μl of the supernatant was removed and used for analysis. Standard curves and quality control samples were prepared in dog plasma from animals not dosed with the prodrug. Samples were analyzed by a partially validated liquid chromatography couple to triple quadrupole mass spectrometry method.

Administration of the citrate salt of the prodrug as a tablet resulted in rapid absorption of the prodrug and the parent compound derived from the prodrug. As summarized in Table 7, plasma exposure to the prodrug and the parent compound was observed following administration. The oral bioavailability of intact prodrug was 11.4%. These results were not markedly different from those observed following oral administration of the prodrug in a solution formulation, illustrating the effectiveness of the tablets containing the citrate salt of the prodrug to deliver the prodrug and its metabolites into the systemic circulation.

TABLE 7

Mean Plasma Pharmacokinetic Parameters for the Prodrug and the Parent Compound Following Oral Administration of a Tablet Formulation of the Citrate Salt of the Prodrug at a mean dose of 3.05 mg/kg equivalents (Mean, n = 3)

| | Value | |
|---|---|---|
| Parameter | Prodrug | Parent Compound |
| $T_{max}$ (hr) | 0.58 | 2.33 |
| $C_{max}$ (nM) | 1,560 | 959 |
| $AUC_{0-t}$ (nM · hr) | 587 | 7,600 |
| $AUC_{0-8}$ (nM · hr) | 608 | 9,630 |
| $t_{1/2}$ (hr) | 0.289 | 11.7 |
| % $F^a$ | 11.4 | Not Determined |

[a]Calculated based on a mean plasma $AUC_{0-t}$ of 818 nM · hr observed following a 30 minute intravenous Infusion of 0.5 mg/kg GS-9131 to beagle dogs.

Example 11

Differential Scanning Calorimetry (DSC) of Citrate, Malonate and Succinate Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate Differential scanning calorimetry accurately measures temperatures and heat flow associated with thermal transitions in a material. The DSC traces of the inventive salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate were generated using a TA Instrument (New Castle, Del.) DSC 2010 at a scan rate of 5° C. $min^{-1}$. FIG. 1 shows the characteristic DSC trace for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram revealed a single endotherm corresponding to the melting point (120.43° C., $\Delta H_f$=73.72 J/g) followed by a single exotherm corresponding to the decomposition of the malonate salt.

Figure 2:
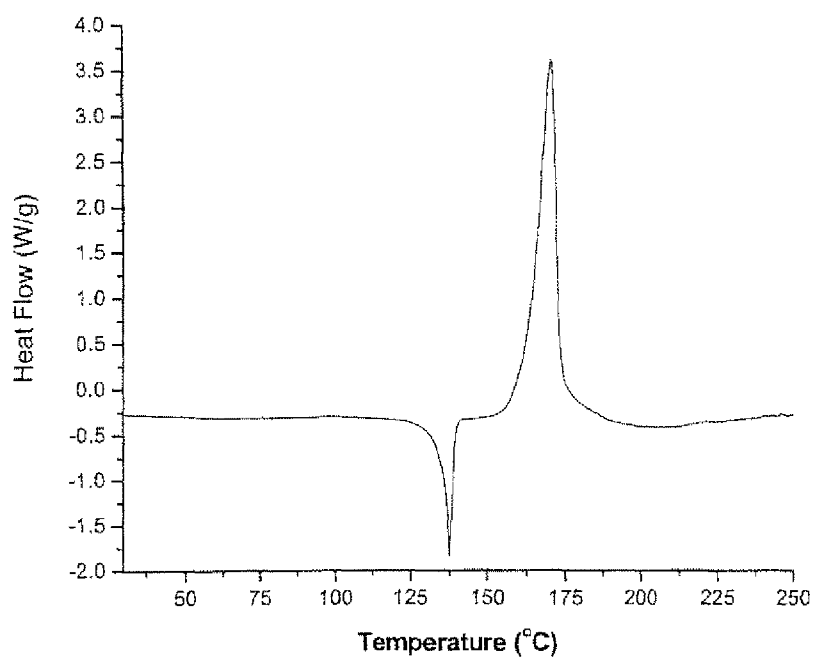
FIG. 2 shows a characteristic DSC trace for the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 2 shows the characteristic DSC trace for the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram of the succinate salt of GS-9131 revealed a single emdotherm corresponding to the melting point (137.44° C., $\Delta H_f$=66.18 J/g) followed by a single exotherm corresponding to the decomposition of the salt.

Figure 3:
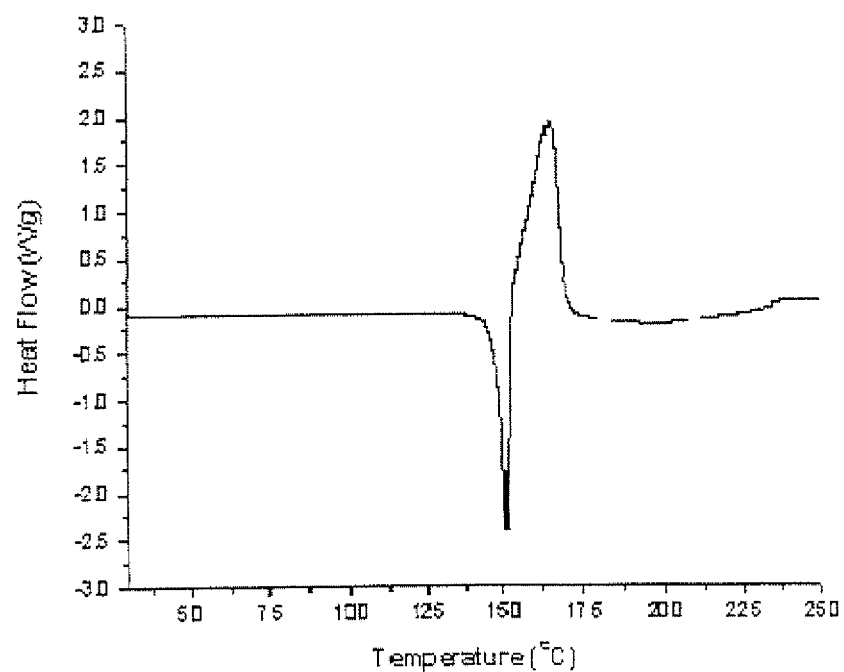
FIG. 3 shows a characteristic DSC trace for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 3 shows the characteristic DSC trace for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate. The DSC thermogram of the citrate salt revealed a single endotherm corresponding to the melting point (149.41° C., $\Delta H_f$=85.72 J/g) followed by a single exotherm corresponding to the decomposition of the citrate salt.

The citrate salt has a significantly greater heat of fusion than the malonate and succinate salts, indicating a higher degree of solid-state crystallinity.

Example 12

X-Ray Diffraction (XRD) Analysis of the Citrate, Malonate and Succinate Salts of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate The X-ray powder diffraction (XRPD) patterns of the inventive salts of Ethyl N—[(S)({[(2R,5R)-5-(6-amino-9H- purin-9-yl)-4-fluoro-2,5-dihydrofuran-2-yl]oxy}methyl) phenoxyphosphinoyl]-L-alaninate were generated using two methods. In the first method, a Shimadzu XRD 6000 instrument with the following attributes was used: Cu X-ray tube, 2.2KW, NE (normal focus); monochromator curved graphite; goniometer vertical, 185 mm radius; divergence slits: 0.5°, 1.0°, 0.05 mm; soller slits: 0.05°, 1°, 2°; receiving slits: 0.15 mm, 0.3 mm; scintillation detector (NaI) HV 500-1200.

In the second method, a Shimadzu XRD 6000 instrument with the following attributes was used: Cu target X-ray tube, 35 kv, current 40 ma; continuous scan, monochromator, divergence slit, 1°; soller slit 1°, receiving slit 0.3 mm.

XRPD data for the malonate and succinate salts were obtained using method 1. XRPD data for the citrate salt was obtained using method 2.

It is understood that experimental deviations can slightly change the XRPD absorption band (peak) information. Thus, the numbers reported in this patent resulting from XRPD patterns of the inventive salts will be the same or essentially the same as the numbers which will occur upon repeating the tests. "Essentially the same" in this context means that typical peak position and intensity variability are taken into account (as they normally would be for any analytical technique). For example, one skilled in the art will appreciate that the peak positions will show some inter-apparatus variability. For example, the 2-theta peak positions typically deviate by as much as 0.1 degrees. Further, one skilled in the art will appreciate that relative peak intensities will also show variability due to the degree of crystallinity, preferred orientation, prepared sample surface, and other factors known in the art. Thus, the relative peak intensities should be taken as qualitative measure only.

Figure 4:
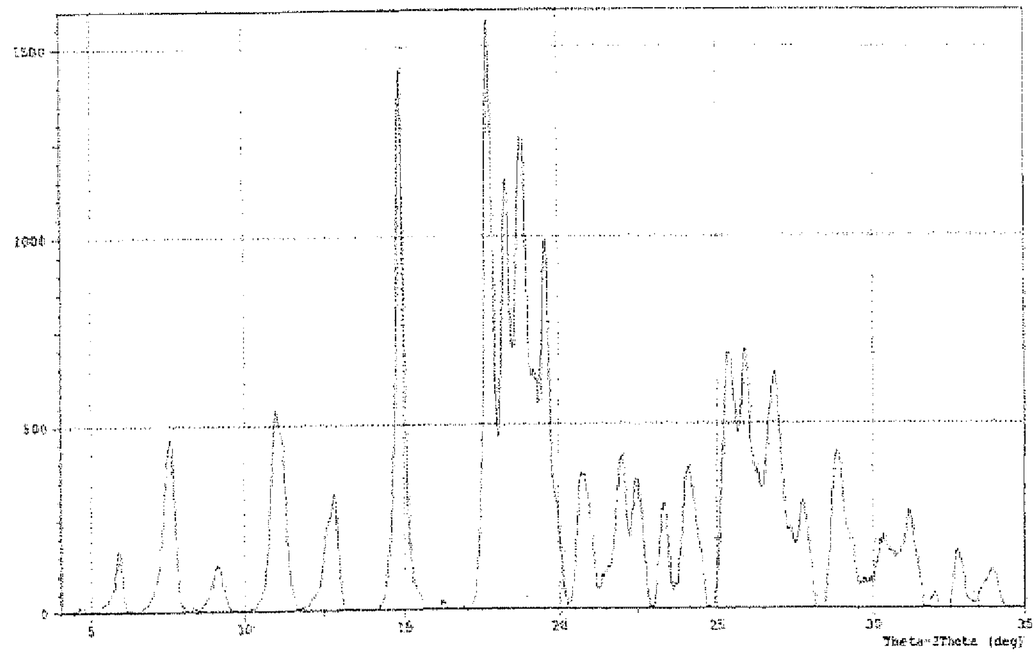
FIG. 4 shows a characteristic X-ray powder diffraction (XRPD) pattern for the malonate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 4 shows the characteristic XRPD pattern for the malonate salt. The principal and characteristic peaks that define this crystalline form of the malonate salt are shown in Tables 8A and 8B.

TABLE 8A

Malonate Salt PXRD Peaks

| Strongest Peaks | 2Theta (deg) | d (A) | FWHM (deg) | Integrated Int |
|---|---|---|---|---|
| 1 | 17.76 | 4.9912 | 0.3190 | 16049 |
| 2 | 14.92 | 5.9342 | 0.3023 | 14513 |
| 3 | 18.80 | 4.7163 | 0.6572 | 21597 |

TABLE 8B

* Basic Data Process *
Group Name
Data Name 34984B
File Name 34984B.PKR
Sample Name Lot# 2587-168-17
Comment Salts USP <941>

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 13 | 17.7561 | 4.99119 | 100 | 0.31900 | 947 | 16049 |
| 2 | 12 | 14.9168 | 5.93423 | 92 | 0.30230 | 867 | 14513 |
| 3 | 15 | 18.8000 | 4.71634 | 80 | 0.65720 | 758 | 21597 |

TABLE 8B-continued

* Basic Data Process *
Group Name
Data Name 34984B
File Name 34984B.PKR
Sample Name Lot# 2587-168-17
Comment Salts USP <941>

Peak Data List

| peak no. | 2Theta (deg) | d (A) | I/I1 | FWHM (deg) | Intensity (Counts) | Integrated Int (Counts) |
|---|---|---|---|---|---|---|
| 1 | 4.7340 | 18.65124 | 1 | 0.16140 | 9 | 69 |
| 2 | 5.9215 | 14.91331 | 11 | 0.26490 | 100 | 1723 |
| 3 | 7.0000 | 12.61783 | 3 | 0.20660 | 29 | 563 |
| 4 | 7.5504 | 11.69922 | 29 | 0.44910 | 279 | 6489 |
| 5 | 9.1500 | 9.65724 | 8 | 0.42000 | 76 | 1779 |
| 6 | 10.5600 | 8.37073 | 4 | 0.18660 | 34 | 468 |
| 7 | 11.0208 | 8.02175 | 34 | 0.29110 | 323 | 4468 |
| 8 | 11.1600 | 7.92200 | 30 | 0.56800 | 287 | 7708 |
| 9 | 12.6400 | 6.99756 | 16 | 0.35600 | 147 | 2545 |
| 10 | 12.8400 | 6.88901 | 20 | 0.27840 | 191 | 2234 |
| 11 | 14.5200 | 6.09549 | 9 | 0.16800 | 87 | 1282 |
| 12 | 14.9168 | 5.93423 | 92 | 0.30230 | 867 | 14513 |
| 13 | 17.7561 | 4.99119 | 100 | 0.31900 | 947 | 16049 |
| 14 | 18.3000 | 4.84405 | 73 | 0.40260 | 692 | 12656 |
| 15 | 18.8000 | 4.71634 | 80 | 0.65720 | 758 | 21597 |
| 16 | 19.2077 | 4.61714 | 41 | 0.36220 | 387 | 6608 |
| 17 | 19.5800 | 4.53018 | 63 | 0.34720 | 593 | 11731 |
| 18 | 20.0200 | 4.43159 | 14 | 0.15560 | 130 | 1783 |
| 19 | 20.7824 | 4.27071 | 24 | 0.54170 | 223 | 6510 |
| 20 | 22.0112 | 4.03499 | 26 | 0.47750 | 250 | 6040 |
| 21 | 22.4800 | 3.95190 | 22 | 0.45260 | 211 | 4333 |
| 22 | 23.3273 | 3.81023 | 18 | 0.29470 | 171 | 2718 |
| 23 | 24.1490 | 3.68242 | 24 | 0.51800 | 232 | 6302 |
| 24 | 25.3800 | 3.50653 | 44 | 0.43120 | 413 | 14100 |
| 25 | 25.8930 | 3.43821 | 44 | 0.27980 | 419 | 5539 |
| 26 | 26.2380 | 3.39378 | 24 | 0.79670 | 227 | 8510 |
| 27 | 26.8200 | 3.32144 | 40 | 0.61720 | 383 | 13675 |
| 28 | 27.3087 | 3.26310 | 14 | 0.49680 | 130 | 3097 |
| 29 | 27.7600 | 3.21107 | 18 | 0.42180 | 175 | 4291 |
| 30 | 28.9185 | 3.08501 | 27 | 0.54570 | 258 | 5924 |
| 31 | 29.3200 | 3.04367 | 11 | 0.30660 | 104 | 2021 |
| 32 | 30.3600 | 2.94173 | 13 | 0.65340 | 119 | 4194 |
| 33 | 31.1400 | 2.86980 | 17 | 0.56000 | 159 | 4356 |
| 34 | 32.0000 | 2.79461 | 3 | 0.14140 | 25 | 165 |
| 35 | 32.8233 | 2.72637 | 10 | 0.39330 | 95 | 1976 |
| 36 | 33.8725 | 2.64428 | 7 | 0.55500 | 64 | 1859 |

Figure 5:
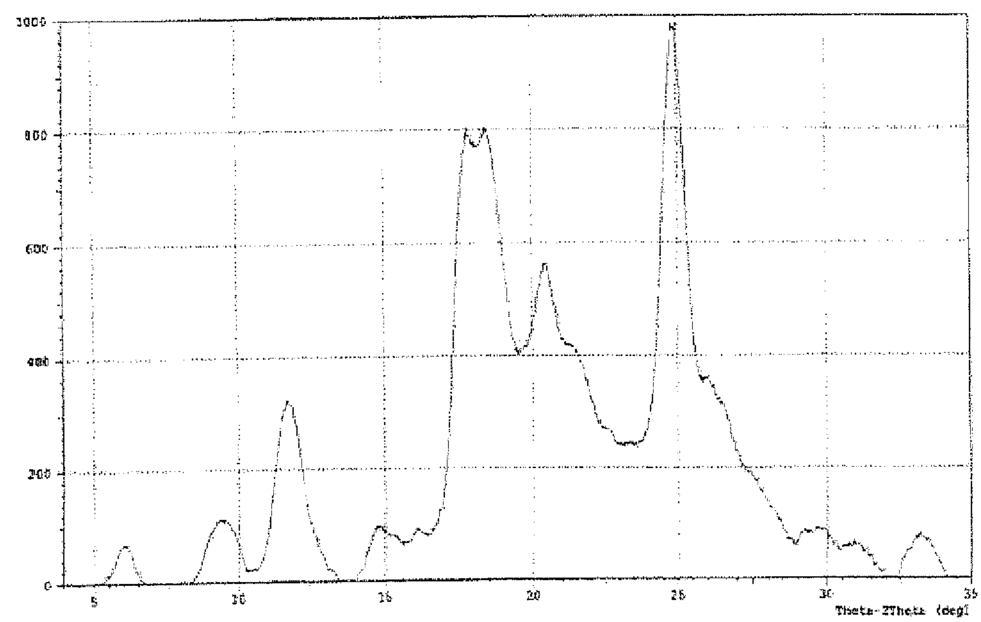
FIG. 5 shows a characteristic XRPD pattern for the succinate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 5 shows the characteristic XRPD pattern or the succinate salt. The principal and characteristic peaks that define this crystalline form of the succinate salt are shown in Tables 9A and 9B.

TABLE 9A

Succinate Salt PXRD Peaks

| Strongest Peaks | 2Theta (deg) | d (A) | FWHM (deg) | Integrated Int |
|---|---|---|---|---|
| 1 | 24.91 | 3.5716 | 1.1300 | 40991 |
| 2 | 18.46 | 4.8024 | 3.7340 | 16639 |
| 3 | 17.76 | 4.9901 | 3.4162 | 9106 |

TABLE 9B

* Basic Data Process *
Group Name
Data Name 34984A
File Name 34984A.PKR
Sample Name Lot# 2587-166-27
Comment Salts USP <941>

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 10 | 24.9100 | 3.57161 | 100 | 1.13000 | 590 | 40991 |
| 2 | 7 | 18.4600 | 4.80243 | 81 | 0.73400 | 480 | 16639 |
| 3 | 6 | 17.7600 | 4.99010 | 79 | 0.41620 | 464 | 9106 |

Peak Data List

| peak no. | 2Theta (deg) | d (A) | I/I1 | FWHM (deg) | Intensity (Counts) | Integrated Int (Counts) |
|---|---|---|---|---|---|---|
| 1 | 6.0033 | 14.71029 | 7 | 0.64670 | 43 | 1492 |
| 2 | 9.4308 | 9.37032 | 12 | 1.24830 | 69 | 4432 |
| 3 | 11.7717 | 7.51169 | 33 | 1.08060 | 195 | 11923 |
| 4 | 14.7400 | 6.00500 | 10 | 0.60000 | 60 | 4288 |
| 5 | 16.0720 | 5.51020 | 9 | 0.55880 | 56 | 1470 |
| 6 | 17.7600 | 4.99010 | 79 | 0.41620 | 464 | 9106 |
| 7 | 18.4600 | 4.80243 | 81 | 0.73400 | 480 | 16639 |
| 8 | 20.4772 | 4.33367 | 57 | 0.87020 | 337 | 13869 |
| 9 | 21.4293 | 4.14323 | 43 | 0.40730 | 252 | 4832 |
| 10 | 24.9100 | 3.57161 | 100 | 1.13000 | 590 | 40991 |
| 11 | 26.1400 | 3.40628 | 36 | 2.92000 | 212 | 21458 |
| 12 | 27.9400 | 3.19079 | 16 | 1.47000 | 86 | 8157 |
| 13 | 29.7800 | 2.99769 | 9 | 0.31340 | 53 | 779 |
| 14 | 30.9200 | 2.88972 | 7 | 1.28000 | 40 | 3619 |
| 15 | 33.2233 | 2.69446 | 8 | 1.08670 | 49 | 2527 |

Figure 6:
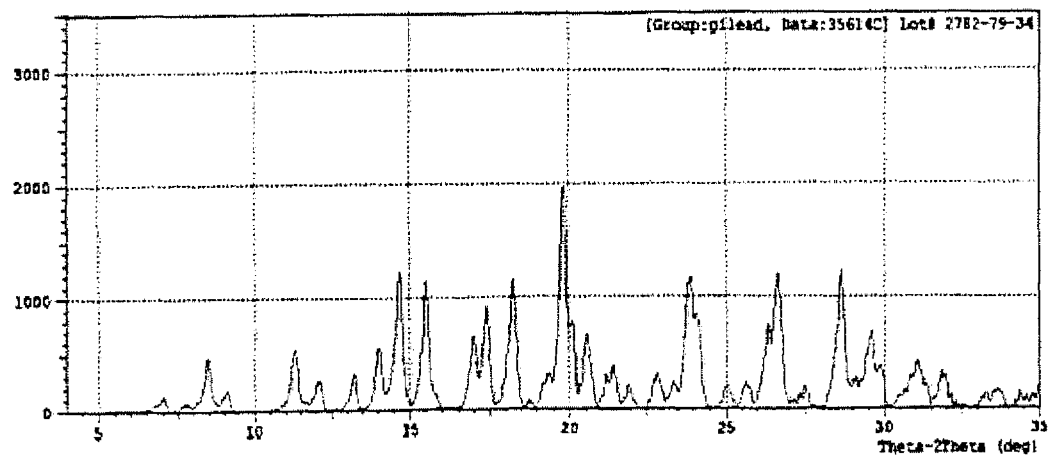
FIG. 6 shows a characteristic XRPD pattern for the citrate salt of Ethyl N—[(S)({[(2R,5R)-5-(6-amino-9H-purin-9-yl)-4-fluoro-2,5-dihydrofuran-2-yl]oxy}methyl)phenoxyphosphinoyl]-L-alaninate.

FIG. 6 shows the characteristic XRPD pattern for the citrate salt. The principal and characteristic peaks that define this crystalline form of the citrate salt are shown in Tables 10A and 10B.

TABLE 10A

| Citrate Salt PXRD Peaks | | | | |
|---|---|---|---|---|
| Strongest Peaks | 2Theta (deg) | d (A) | FWHM (deg) | Integrated Int |
| 1 | 19.81 | 4.4784 | 0.2635 | 14837 |
| 2 | 28.63 | 3.1155 | 0.3312 | 13074 |
| 3 | 14.64 | 6.0465 | 0.2473 | 10572 |

TABLE 10B

* Basic Data Process *
Group Name
Data Name 35614A
File Name 35614A.PKR
Sample Name Lot# 2782-78-32
Comment USP <941>

Strongest 3 peaks

| no. | peak no. | 2Theta (deg) | d (A) | I/I1 | FWHM (deg) | Intensity (Counts) | Integrated Int (Counts) |
|---|---|---|---|---|---|---|---|
| 1 | 21 | 19.7858 | 4.48352 | 100 | 0.26810 | 1443 | 20538 |
| 2 | 30 | 23.8400 | 3.72944 | 55 | 0.33400 | 793 | 14567 |
| 3 | 35 | 26.5965 | 3.34884 | 51 | 0.31810 | 734 | 11131 |

TABLE 10B-continued

* Basic Data Process *
Group Name
Data Name 35614A
File Name 35614A.PKR
Sample Name Lot# 2782-78-32
Comment USP <941>

Peak Data List

| peak no. | 2Theta (deg) | d (A) | I/I1 | FWHM (deg) | Intensity (Counts) | Integrated Int (Counts) |
|---|---|---|---|---|---|---|
| 1 | 6.7400 | 13.10398 | 3 | 0.16360 | 47 | 456 |
| 2 | 6.9496 | 12.70922 | 6 | 0.21930 | 87 | 864 |
| 3 | 8.2200 | 10.74764 | 6 | 0.23120 | 81 | 1414 |
| 4 | 8.4436 | 10.46352 | 18 | 0.22630 | 253 | 2802 |
| 5 | 9.0566 | 9.75662 | 6 | 0.22460 | 89 | 1275 |
| 6 | 11.0600 | 7.99341 | 4 | 0.18000 | 62 | 762 |
| 7 | 11.2871 | 7.83308 | 16 | 0.23720 | 238 | 2770 |
| 8 | 11.8800 | 7.44345 | 4 | 0.19560 | 52 | 603 |
| 9 | 12.0508 | 7.33833 | 8 | 0.25030 | 114 | 1167 |
| 10 | 13.1691 | 6.71758 | 16 | 0.22170 | 229 | 3085 |
| 11 | 13.9959 | 6.32255 | 25 | 0.23910 | 358 | 5182 |
| 12 | 14.6151 | 6.05604 | 33 | 0.26400 | 470 | 7221 |
| 13 | 15.4624 | 5.72604 | 25 | 0.30010 | 356 | 5658 |
| 14 | 15.8200 | 5.59740 | 3 | 0.18800 | 48 | 832 |
| 15 | 16.9600 | 5.22364 | 26 | 0.27100 | 377 | 5496 |
| 16 | 17.3474 | 5.10785 | 46 | 0.26120 | 668 | 9289 |
| 17 | 18.0000 | 4.92411 | 19 | 0.19920 | 271 | 3037 |
| 18 | 18.2200 | 4.86514 | 32 | 0.20420 | 465 | 5224 |
| 19 | 18.7154 | 4.73746 | 4 | 0.21420 | 51 | 606 |
| 20 | 19.2200 | 4.61421 | 10 | 0.19200 | 146 | 2871 |
| 21 | 19.7858 | 4.48352 | 100 | 0.26810 | 1443 | 20538 |
| 22 | 20.0800 | 4.41849 | 38 | 0.19380 | 546 | 6060 |
| 23 | 20.5315 | 4.32233 | 32 | 0.32250 | 455 | 7724 |
| 24 | 21.1200 | 4.20320 | 8 | 0.25500 | 114 | 1667 |
| 25 | 21.4000 | 4.14883 | 16 | 0.26760 | 235 | 3054 |
| 26 | 21.8913 | 4.05682 | 10 | 0.26260 | 141 | 2250 |
| 27 | 22.8001 | 3.89713 | 13 | 0.30110 | 181 | 2641 |
| 28 | 23.2200 | 3.82760 | 3 | 0.19760 | 50 | 746 |
| 29 | 23.3691 | 3.80351 | 6 | 0.16040 | 83 | 625 |
| 30 | 23.8400 | 3.72944 | 55 | 0.33400 | 793 | 14567 |
| 31 | 24.1800 | 3.67776 | 26 | 0.12300 | 380 | 4146 |
| 32 | 25.0296 | 3.55482 | 8 | 0.32290 | 119 | 2002 |
| 33 | 25.6031 | 3.47648 | 7 | 0.22090 | 102 | 1365 |
| 34 | 26.2800 | 3.38845 | 26 | 0.30180 | 379 | 5681 |
| 35 | 26.5965 | 3.34884 | 51 | 0.31810 | 734 | 11131 |
| 36 | 27.4848 | 3.24259 | 6 | 0.20170 | 83 | 1222 |
| 37 | 28.1600 | 3.16636 | 4 | 0.09340 | 58 | 441 |
| 38 | 28.5989 | 3.11875 | 46 | 0.33280 | 666 | 12909 |
| 39 | 29.0484 | 3.07151 | 9 | 0.23960 | 127 | 1440 |
| 40 | 29.5600 | 3.01950 | 20 | 0.48340 | 290 | 6624 |
| 41 | 29.8800 | 2.98789 | 16 | 0.14600 | 235 | 2012 |
| 42 | 30.4400 | 2.93419 | 3 | 0.09340 | 44 | 274 |
| 43 | 30.7800 | 2.90254 | 11 | 0.10020 | 155 | 737 |
| 44 | 31.0600 | 2.87701 | 16 | 0.19060 | 233 | 3504 |
| 45 | 31.3400 | 2.85195 | 4 | 0.18000 | 55 | 802 |
| 46 | 31.5800 | 2.83082 | 4 | 0.12960 | 54 | 357 |
| 47 | 31.8602 | 2.80656 | 12 | 0.36550 | 172 | 2804 |
| 48 | 32.2200 | 2.77603 | 4 | 0.08580 | 55 | 482 |
| 49 | 33.0800 | 2.70580 | 3 | 0.09060 | 50 | 388 |
| 50 | 33.2668 | 2.69103 | 5 | 0.12920 | 65 | 453 |
| 51 | 33.6921 | 2.66571 | 7 | 0.36940 | 108 | 2008 |
| 52 | 34.3755 | 2.60673 | 6 | 0.15550 | 83 | 1053 |

All literature and patent citations above are hereby expressly incorporated by reference at the locations of their citation. Specifically cited sections or pages of the above cited works are incorporated by reference with specificity. While the invention has been described in detail sufficient to allow one of ordinary skill in the art to make and use the subject matter of the following claims, it is also contemplated that certain modifications of the following claims can be made and yet remain within the scope and spirit of the invention.

What is claimed is:

1. A citrate salt of formula I or a hydrate thereof:

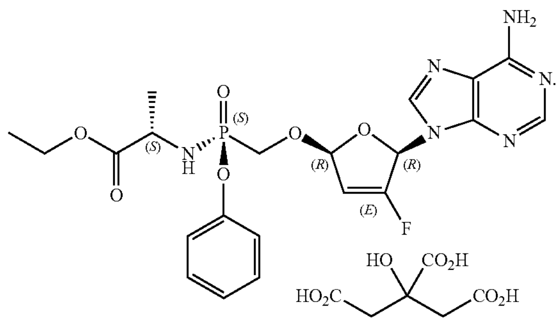

2. The salt or hydrate of claim 1, characterized by being crystalline.

3. The salt of claim 2, characterized by spectral d-spacing absorption bands obtained from an X-ray powder diffraction pattern of the same or essentially the same as 4.48, 3.12 and 6.05 angstroms.

4. The salt of claim 2, characterized by 2-theta diffraction angle absorption bands obtained from an X-ray powder diffraction pattern of the same or essentially the same as 19.81, 28.63 and 14.64 degrees.

5. The hydrate of claim 2, characterized in being partially or fully hydrated.

6. The salt of claim 2, characterized in being anhydrous or essentially anhydrous.

7. A pharmaceutical composition comprising a therapeutically effective amount of the salt or hydrate of claim 1 and a pharmaceutically acceptable carrier or excipient.

8. The pharmaceutical composition of claim 7, further comprising an additional therapeutic agent.

9. The pharmaceutical composition of claim 8, wherein the additional therapeutic agent is an anti-HIV drug.

10. The pharmaceutical composition of claim 7, wherein the pharmaceutical composition is in a unit dosage form.

11. The pharmaceutical composition of claim 10, wherein the unit dosage form is a tablet.

12. A succinate salt of formula II or a hydrate thereof:

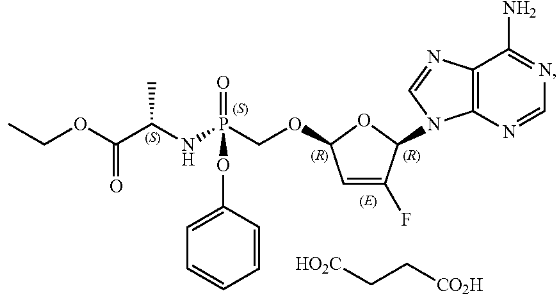

characterized as being crystalline.

13. The salt of claim 12, characterized by spectral d-spacing absorption bands obtained from an X-ray powder diffraction pattern of the same or essentially the same as 3.57, 4.80 and 4.99 angstroms.

14. The salt of claim 12, characterized by 2-theta diffraction angle absorption bands obtained form an X-ray powder diffraction pattern of the same or essentially the same as 24.91, 18.46 and 17.76 degrees.

15. A pharmaceutical composition comprising a therapeutically effective amount of the salt or hydrate of claim 12 and a pharmaceutically acceptable carrier or excipient.

16. The pharmaceutical composition of claim 15, further comprising an additional active ingredient.

17. A malonate salt of formula III or a hydrate thereof:

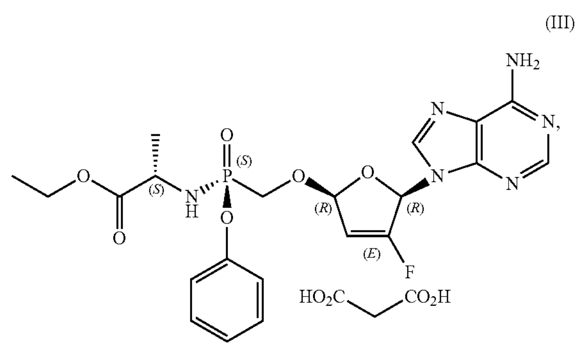

characterized as being crystalline.

18. The salt of claim 17, characterized by spectral d-spacing absorption bands obtained from an X-ray powder diffraction pattern of the same or essentially the same as 4.99, 5.93 and 4.72 angstroms.

19. The salt of claim 17, characterized by 2-theta diffraction angle absorption bands obtained from an X-ray powder diffraction pattern of the same or essentially the same as 17.76, 14.92 and 18.80 degrees.

20. A pharmaceutical composition comprising a therapeutically effective amount of the salt or hydrate of claim 17 and a pharmaceutically acceptable carrier or excipient.

21. The pharmaceutical composition of claim 20, further comprising an additional active ingredient.

* * * * *